(12) United States Patent
Bellomo et al.

(10) Patent No.: US 8,685,635 B2
(45) Date of Patent: **\*Apr. 1, 2014**

(54) DERMAL MICRO-ORGANS, METHODS AND APPARATUSES FOR PRODUCING AND USING THE SAME

(71) Applicant: Medgenics Medical Israel Ltd., Misgav (IL)

(72) Inventors: Stephen F. Bellomo, Zichron Yaakov (IL); Itzhak Lippin, Moshav Beit Yitzhak (IL); Guillermo Alberto Piva, San Ramon, CA (US); Lior Rosenberg, Omer (IL); Mordechay Bukhman, Carmiel (IL); Baruch S. Stern, Haifa (IL); David Shalhevet, Kiryat Tivon (IL); Menachem D. Shavitt, D.N. Misgav (IL); Andrew L. Pearlman, D.N. Misgav (IL); Noam Shani, Zichron Yaakov (IL); Einat Almon, Timrat (IL)

(73) Assignee: Medgenics Medical Israel Ltd., Misgav (IL)

( \* ) Notice: Subject to any disclaimer, the term of this patent is extended or adjusted under 35 U.S.C. 154(b) by 0 days.

This patent is subject to a terminal disclaimer.

(21) Appl. No.: 13/656,832

(22) Filed: Oct. 22, 2012

(65) Prior Publication Data

US 2013/0052240 A1   Feb. 28, 2013

Related U.S. Application Data

(63) Continuation of application No. 13/166,821, filed on Jun. 23, 2011, now Pat. No. 8,293,463, which is a continuation of application No. 12/216,321, filed on Jul. 2, 2008, now Pat. No. 8,142,990, which is a continuation of application No. 10/834,345, filed on Apr. 29, 2004, now Pat. No. 7,468,242, and a continuation-in-part of application No. PCT/IL02/00877, filed on Nov. 5, 2002, and a continuation-in-part of application No. PCT/IL02/00878, filed on Nov. 5, 2002, and a continuation-in-part of application No. PCT/IL02/00879, filed on Nov. 5, 2002, and a continuation-in-part of application No. PCT/IL02/00880, filed on Nov. 5, 2002.

(60) Provisional application No. 60/466,793, filed on May 1, 2003, provisional application No. 60/492,754, filed on Aug. 6, 2003.

(51) Int. Cl.
 *A01N 1/00*  (2006.01)
 *C12N 5/00*  (2006.01)
 *A61F 2/10*  (2006.01)

(52) U.S. Cl.
 USPC .......................... 435/1.1; 435/325; 623/15.11

(58) Field of Classification Search
 USPC .................................. 435/1.1, 325; 623/15.11
 See application file for complete search history.

(56) References Cited

U.S. PATENT DOCUMENTS

| | | |
|---|---|---|
| 376,511 A | 1/1888 | Carter |
| 1,516,071 A | 11/1924 | Apolant |
| 3,076,461 A | 2/1963 | Meek et al. |
| 3,470,782 A | 10/1969 | Acker |
| 3,613,242 A | 10/1971 | Hill et al. |
| 4,353,888 A | 10/1982 | Sefton |
| 4,391,909 A | 7/1983 | Lim |
| 4,773,418 A | 9/1988 | Hettich |
| 4,883,666 A | 11/1989 | Sabel et al. |
| 4,892,538 A | 1/1990 | Aebischer et al. |
| 5,106,627 A | 4/1992 | Aebischer et al. |
| 5,266,480 A | 11/1993 | Naughton et al. |
| 5,423,330 A | 6/1995 | Lee |
| 5,477,862 A | 12/1995 | Haaga |
| 5,670,148 A | 9/1997 | Sherwin et al. |
| 5,693,064 A | 12/1997 | Arnold |
| 5,817,120 A | 10/1998 | Rassman |

(Continued)

FOREIGN PATENT DOCUMENTS

| | | |
|---|---|---|
| CA | 2279996 | 7/1998 |
| DE | 29 39 057 | 4/1981 |

(Continued)

OTHER PUBLICATIONS

Rubanyi, "The Future of Human Gene Therapy" Molecular Aspects of Medicine, 22:113-142, (2001).
Orive et al. "Cell encapsulation: Promise and progress" Nature Medicine. 9(1):104-107, (2003).
Brill-Almon E. et al: "Ex vivo transduction of human dermal tissue structure for autologues implantation production and delivery of therapeutic proteins," Molecule Therapy, Academic Press CA, USA, vol. 12, No. 2, pp. 274-282, (2005).
Hasson E. et al. "Solid tissues can be manipulated ex vivo and used as vehicles for gene therapy" Journal of Gene Medicine, vol. 7(7), pp. 923-935 (2005).

(Continued)

*Primary Examiner* — Marcia S Noble
(74) *Attorney, Agent, or Firm* — Mark S. Cohen; Pearl Cohen Zedek Latzer Baratz LLP

(57) ABSTRACT

Embodiments of the present invention provide Dermal Micro-organs (DMOs), methods and apparatuses for producing the same. Some embodiments of the invention provide a DMO including a plurality of dermal components, which substantially retain the micro-architecture and three dimensional structure of the dermal tissue from which they are derived, having dimensions selected so as to allow passive diffusion of adequate nutrients and gases to cells of the DMO and diffusion of cellular waste out of the cells so as to minimize cellular toxicity and concomitant death due to insufficient nutrition and accumulation of waste in the DMO. Some embodiments of the invention provide methods and apparatuses for harvesting the DMO. An apparatus for harvesting the DMO may include, according to some exemplary embodiments, a support configuration to support a skin-related tissue structure from which the DMO is to be harvested, and a cutting tool able to separate the DMO from the skin-related tissue structure. Other embodiments are described and claimed.

15 Claims, 20 Drawing Sheets

(56) References Cited

U.S. PATENT DOCUMENTS

| | | | |
|---|---|---|---|
| 5,871,767 | A | 2/1999 | Dionne et al. |
| 5,888,720 | A | 3/1999 | Mitrani |
| 5,932,459 | A | 8/1999 | Sittinger et al. |
| 5,944,673 | A | 8/1999 | Gregoire et al. |
| 6,001,647 | A | 12/1999 | Peck et al. |
| 6,027,512 | A | 2/2000 | Bridges |
| 6,036,657 | A | 3/2000 | Milliman et al. |
| 6,039,760 | A | 3/2000 | Eisenberg |
| 6,197,575 | B1 | 3/2001 | Griffith et al. |
| 6,303,136 | B1 | 10/2001 | Li et al. |
| 6,372,482 | B1 | 4/2002 | Mitarni |
| 6,472,200 | B1 | 10/2002 | Mitrani |
| 6,485,721 | B1 | 11/2002 | Yoshida et al. |
| 7,067,496 | B2 | 6/2006 | Saito et al. |
| 7,468,242 | B2 | 12/2008 | Bellomo et al. |
| 7,625,384 | B2 | 12/2009 | Eriksson et al. |
| 7,666,134 | B2 | 2/2010 | Eriksson et al. |
| 7,708,746 | B2 | 5/2010 | Eriksson et al. |
| 2002/0001580 | A1 | 1/2002 | Hermonat et al. |
| 2002/0068880 | A1 | 6/2002 | Burbank et al. |
| 2003/0086914 | A1 | 5/2003 | Mitarni |
| 2003/0152561 | A1 | 8/2003 | Mitrani |
| 2003/0152562 | A1 | 8/2003 | Mitrani |
| 2003/0157074 | A1 | 8/2003 | Mitrani |
| 2004/0172045 | A1 | 9/2004 | Eriksson et al. |
| 2004/0230215 | A1 | 11/2004 | Eriksson et al. |
| 2006/0271070 | A1 | 11/2006 | Eriksson et al. |
| 2007/0038236 | A1 | 2/2007 | Cohen |
| 2010/0042127 | A1 | 2/2010 | Eriksson et al. |
| 2010/0145360 | A1 | 6/2010 | Eriksson et al. |
| 2011/0264115 | A1 | 10/2011 | Asrani |

FOREIGN PATENT DOCUMENTS

| | | |
|---|---|---|
| DE | 34 32 897 | 3/1986 |
| EP | 1358857 | 11/2003 |
| JP | 233694/86 | 10/1986 |
| JP | 76399/99 | 3/1999 |
| JP | 2003-176213 | 6/2003 |
| JP | 2005/506084 | 3/2005 |
| JP | 08/196271 | 8/2008 |
| WO | WO 96/15225 | 5/1996 |
| WO | WO 9704720 | 2/1997 |
| WO | WO 97/08295 | 3/1997 |
| WO | WO 9715655 | 5/1997 |
| WO | WO 98/16158 | 5/1998 |
| WO | WO 99/49807 | 7/1999 |
| WO | WO 99/43270 | 9/1999 |
| WO | WO 01/00859 | 1/2001 |
| WO | WO 01/07098 | 2/2001 |
| WO | WO 01/08714 | 2/2001 |
| WO | WO 01/60424 | 8/2001 |
| WO | WO 03/002154 | 1/2003 |
| WO | WO 03/006669 | 1/2003 |
| WO | WO 03/020107 | 3/2003 |
| WO | 1306426 | 5/2003 |
| WO | WO 03/035851 | 5/2003 |
| WO | WO 03/039382 | 5/2003 |
| WO | WO/03049626 | 6/2003 |
| WO | WO 03/060062 | 7/2003 |
| WO | WO 2004/075764 | 9/2004 |
| WO | WO 2004/099363 | 11/2004 |
| WO | WO 2005/033273 | 4/2005 |
| WO | WO 2006/110843 | 10/2006 |
| WO | WO 2007/117488 | 10/2007 |
| WO | WO 99/06073 | 2/2009 |
| WO | WO 2011/140497 | 11/2011 |

OTHER PUBLICATIONS

Uitto et al. "Skin elastic fibres: regulation of human elastin promoter activity in transgenic mice" Ciba Foundation Symposium, vol. 192, p. 237-253 (1995).

Wang et al. "Transgenic studies with a keratin promoter-driven growth formone transgene prospects for gene therapy" Proc Natl Acad Sci U S A, 4(1):219-26. 1, Jan. 7, 1997.

Supplementary European Search Report Aplication No. 04760621.5 Date of Mailing Apr. 27, 2009.

International Search Report Application No. PCT/US04/13194 Date of mailing Mar. 18, 2005.

Jaakkola et al. "Transcriptional targeting of adenoviral gene delivery into migrating wound keratinocytes using fire, a growth factor—inducible regulatory element" Gene Therapy 7:1640-1647, (2000).

Palmer et al. "Genetically modified skin fibroblasts persist long after transplantation but gradually inactive introduced genes" Proc. Natl. Acad. Sci. USA vol. 88, pp. 1330-1334. Cell Biology, Feb. 1991.

Ng et al. "Requirement of an AP—1 site in the Calcium Response Region of the Involuerin Promoter" JBC 275(31): 24080-24088, (2000).

Suzuki et al. "Identification of the hepatocyte mitogen in bovina spleen as heparin-binding growth factors" Biochemical and Biophysical Research Communications vol. 186, Issue 3, pp. 1192-1200, Aug. 14, 1992.

Sato H et al. "Repression of P53-Dependent Sequence-Specific Transactivation by MEF2C" Biochemical and Biophysical Research Communications vol. 214, Issue 2, pp. 468-474, Sep. 14, 1995.

Auerbach et al, "Angiogenesis Induction by Tumors, Embryonic Tissues, and Lymphocyte" Cancer Res; 36:3435-3440. (1976).

Swanson et al. "Characterization of myocyte enhancer factor 2 (MEF2) expression in B and T cells. MEF2C is a B cell-restricted transcription factor in lymphocytes" Molecular Immunology vol. 35, Issue 8, pp. 445-456, pp. 445-456, May 1, 1998.

Aoki Y et al. "Angiogenesis and hematopoiesis induced by Kaposi's sarcoma-associated herpesvirus-encoded interleukin-6" Blood. 93:4034-4043. (1999).

Shifren et al. "In the human fetus, vascular endothelial growth factor is expressed in epithelial cells and myocytes, but not vascular endothelium implications for mode of action" The Journal of Clinical Endocrinology & Metabolism Jul. 1, vol. 79 No. 1 316-322. (1994).

Upreti et al. "Preparation of representative homogenates of biological tissues: Effect of salt on protein extraction" Analytical vol. 198, Issue 2, pp. 298-301, Nov. 1, 1991.

Eming et al. "Genetically Modified Human Keratinocytes Overexpressing PDGF-A Enhance the Performance of a Composite Skin Graft" Human Gene Therapy. 9(4); 529-539. Mar. 1998.

Gunther et al. Specific targets in tumor tissue for the delivery of therapeutic genes. Curr Med Chem Anti-cancer Agents 5: 157-171, (2005).

Azimzadeh et al. "Xenograft rejection: molecular mechanisms and therapeutic prospects" Hematology and Cell Therapy vol. 36, No. 4, 331-343, (1996).

Gould and Auchincloss. "Direct and indirect recognition: the role of MHC antigens in graft rejection" Immunol Toay. 20(2):77-82 Feb. 1999.

Printout from www.hemophilia.org/NhFWeb/MainPgs/MainNHF. aspxmenuid+180&contentid=45, pp. 1-2, printed Apr. 17, 2012.

Chao et al. "Sustained expression of human factor VIII in mice using a parvovirus-based vector" Blood, vol. 95, No. 5 pp. 1594-1599, Mar. 1, 2000.

Mitrani et al. "Biopump Autologous skin-derives micro-organ genetically engineered to provide sustained continous secretion of therapeutic proteins" Dermatologic Therapy, vol. 24, 489-497,(2011).

International Search Report Application PCT/IL2012/050482 Date of Mailing Apr. 2, 2013.

1

DERMAL MICRO-ORGANS, METHODS AND APPARATUSES FOR PRODUCING AND USING THE SAME

CROSS REFERENCE TO RELATED APPLICATIONS

This application is a Continuation of U.S. application Ser. No. 13/166,821, filed on Jun. 23, 2011, which is a Continuation of U.S. application Ser. No. 12/216,321, filed on Jul. 2, 2008, which is a Continuation of U.S. application Ser. No. 10/834,345, filed Apr. 29, 2004, now U.S. Pat. No. 7,468,242, which claims priority from U.S. Provisional Application No. 60/466,793, filed May 1, 2003, and U.S. Provisional Application No. 60/492,754, filed Aug. 6, 2003; and is a Continuation in Part of PCT International Application Numbers PCT/IL02/00877, PCT/IL02/00878, PCT/IL02/00879 and PCT/IL02/00880, all filed Nov. 5, 2002, which claim priority from U.S. Provisional Application No. 60/330,959, filed Nov. 5, 2001, U.S. Provisional Application No. 60/393,745, filed Jul. 8, 2002 and U.S. Provisional Application No. 60/393,746, filed Jul. 8, 2002, all of which are incorporated herein by reference, in their entirety.

FIELD OF THE INVENTION

The invention relates to the field of tissue based micro organs, therapeutic tissue based micro organs and methods and apparatuses for harvesting, processing, implanting and manipulating dermal tissue.

BACKGROUND OF THE INVENTION

Various methods for delivering therapeutic agents are known. For example, therapeutic agents can be delivered orally, transdermally, by inhalation, by injection and by depot with slow release. In each of these cases the method of delivery is limited by the body processes that the agent is subjected to, by the requirement for frequent administration, and limitations on the size of molecules that can be utilized. For some of the methods, the amount of therapeutic agent varies between administrations.

A dermal micro-organ (DMO), which can be sustained outside the body ("ex vivo" or "in vitro") in an autonomously functional state for an extended period of time, and to which various manipulations can be applied, may then be implanted subcutaneously or within the body for the purpose of treating diseases, or disorders, or for plastic surgical purposes. The DMO can be modified to express a gene product of interest. These modified dermal micro-organs are generally referred to as Dermal Therapeutic Micro-Organs (DTMOs).

Skin micro-organs, including layers of epidermal and dermal tissues, for example; as outlined in PCT/IL02/0880, have been observed to be associated with a number of clinical challenges. Harvesting of a skin sample leaves a superficial wound on the patient that may last several weeks and may leave scars. The harvested skin sample requires significant processing to generate micro-organs from this sample. Also, implantation of skin micro-organs subcutaneously or deeper in the body have been found to result in the development of keratin cysts or keratin micro-cysts. Additionally, implantation of skin micro-organs as a graft onto the skin surface in "slits" requires significant technical expertise in order to handle the MO while maintaining its proper orientation.

Harvesting of dermis, e.g., to be used as a "filler material" in a plastic surgical or cosmetic procedure, is known in the art. Conventional harvesting techniques include using a dermatome or scalpel to peel away a layer of epidermis in order to expose a section of dermis. The dermatome or scalpel may then be used again to manually harvest the exposed section of dermis.

Another conventional apparatus for harvesting dermis, albeit not commonly used, is the Martin Dermal Harvester marketed by Padgett (Part No. P-225) for the indication of harvesting dermal cores from the back for subsequent implantation into the lips during cosmetic lip augmentation procedures. To operate this device, which is not commonly used, a sharpened cutting tube, which includes a reusable thick walled tube with an inner diameter of approximately 4.5 mm, is manually rotated at a very slow speed. Using this type of device generally requires applying pressure to the skin surface directly above the harvest site and installing sutures with active tugging as the cutting tube is pushed forward. Furthermore, the resulting harvested dermis is generally not uniform in dimensions and includes "plugs" of epidermis at either end of the dermal core.

SUMMARY OF THE INVENTION

Embodiments of some aspects of the present invention provide a DMO/DTMO with the ability to be maintained ex-vivo in a generally viable state, which may allow various manipulations to be performed on the DMO, while keeping a high production and secretion level of the desired therapeutic agent. In addition, embodiments of some aspects of the present invention provide a method of harvesting a DMO and subsequently implanting a DTMO without forming keratin cysts or keratin microcysts, e.g., upon implantation of the DTMO subcutaneously or deeper in the body. Furthermore, it will be appreciated by persons skilled in the art that the methods and devices according to some embodiments of the present invention may be relatively uncomplicated and, therefore, the level of skill required from a professional to carry out the methods and/or to use the devices of the present invention may not be as demanding as those required in conventional procedures.

Some exemplary embodiments of the invention provide a dermal micro-organ (DMO) having a plurality of dermal components, which may include cells of the dermal tissue and a surrounding matrix. The DMO according to embodiments of the invention may generally retain a micro-architecture and three dimensional structure of the dermal organ from which it is obtained and the dimensions of the DMO may allow passive diffusion of adequate nutrients and gases to the cells and diffusion of cellular waste out of the cells so as to minimize cellular toxicity and concomitant death due to insufficient nutrition and accumulation of waste.

In some exemplary embodiments of the invention, the dermal micro-organ of the invention does not produce keratin or produces negligible amounts of keratin.

In some embodiments of the invention, the dermal micro-organ does not produce keratin and/or keratin cysts following subcutaneous or deeper implantation in a body.

In another embodiment of the invention, the dermal micro-organ of the invention produces micro keratin cysts following that will atrophy within a relatively short period of time, e.g., days or weeks after subcutaneous implantation.

In another embodiment of the invention, the dermal micro-organ of the invention contains hair follicles and sebaceous glands, which will atrophy after a short period of time, e.g., days or weeks.

In another embodiment of the invention, the dermal micro-organ of the invention contains glands that will connect to the skin surface after a short period of time, e.g., days or weeks.

Further exemplary embodiments of the invention provide a method and apparatus of harvesting a dermal micro-organ. The method may include stabilizing and/or supporting a skin-related tissue structure from which a dermal micro-organ is to be harvested, e.g., such that the skin-related tissue structure is maintained at a desired shape and/or position, separating at least a portion of the dermal micro-organ from the skin-related tissue structure, and isolating the separated dermal micro-organ from the body. According to some of these exemplary embodiments, the support configuration may include a first tubular element, and the cutting tool may include a second tubular element adapted to be inserted along and substantially coaxially with the first element. According to other exemplary embodiments, the support configuration may include a vacuum chamber having an inner support surface able to maintain the skin-related tissue structure at a desired shape and/or position to enable the cutting tool to separate the DMO from the skin-related tissue structure.

Further exemplary embodiments of the invention provide a genetically modified dermal micro-organ expressing at least one recombinant gene product the dermal micro-organ having a plurality of dermal components, including cells and matrix of the dermal tissue, which retain the micro-architecture and three dimensional structure of the dermal tissue from which they are obtained, and having dimensions selected so as to allow passive diffusion of adequate nutrients and gases to the cells and diffusion of cellular waste out of the cells so as to minimize cellular toxicity and concomitant death due to insufficient nutrition and accumulation of waste, wherein at least some of the cells of the dermal micro-organ express at least one recombinant gene product or at least a portion of said at least one recombinant gene product.

Yet further exemplary embodiments the invention provide a genetically modified dermal micro-organ expressing at least one recombinant protein, the dermal micro-organ having a plurality of dermal components, including cells and matrix of the dermal tissue, which retain the micro-architecture and three dimensional structure of the dermal tissue from which they are obtained, and having dimensions selected so as to allow passive diffusion of adequate nutrients and gases to the cells and diffusion of cellular waste out of then cells so as to minimize cellular toxicity and concomitant death due to insufficient nutrition and accumulation of waste, wherein at least some of the cells of the dermal micro-organ express at least a portion of at least one recombinant protein.

In some embodiments of the invention, the genetically modified dermal micro-organ of the invention produces substantially no keratin.

In some embodiments, the invention provides a method of delivering to a recipient a recombinant gene product produced by the dermal micro-organ.

In some embodiments, the invention provides a method of inducing a local or systemic physiological effect by implanting a dermal micro-organ in a recipient.

In another embodiment the invention provides a method of delivering a protein of interest to a subject. The method includes implanting the genetically modified dermal micro-organ into the skin, under the skin or at other locations in the body.

In another embodiment, the invention provides a method of implanting a dermal micro-organ so as to avoid or to reduce keratin cyst formation.

BRIEF DESCRIPTION OF THE DRAWINGS

Non-limiting embodiments of the invention are described in the following description, to be read with reference to the figures attached hereto. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale.

DETAILED DESCRIPTION OF EXEMPLARY EMBODIMENTS

Figure 1:
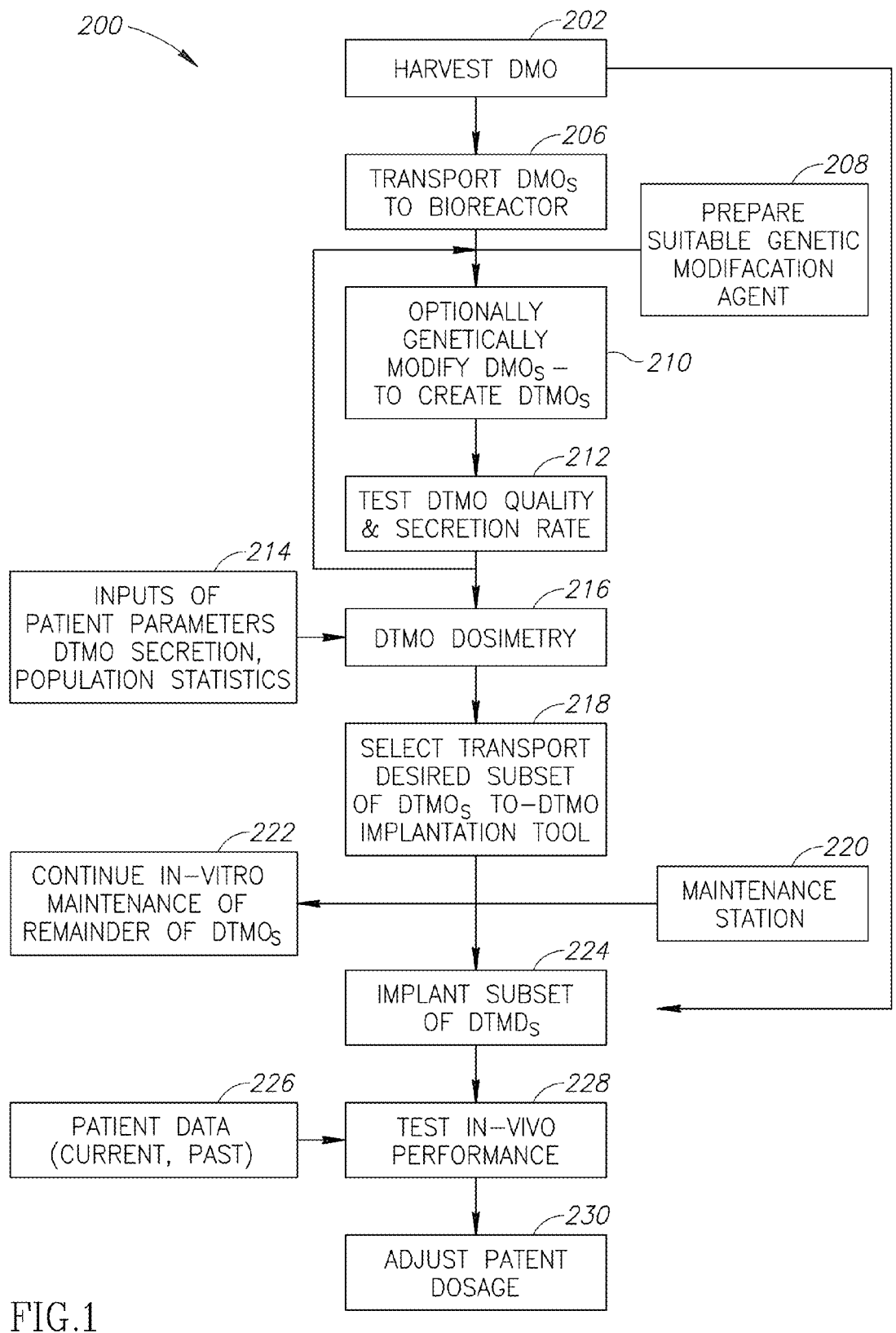
FIG. 1 is a schematic block diagram of an exemplary method of producing and utilizing dermal therapeutic micro-organs (DTMOs), in accordance with an exemplary embodiment of the invention.
Figure 2A:
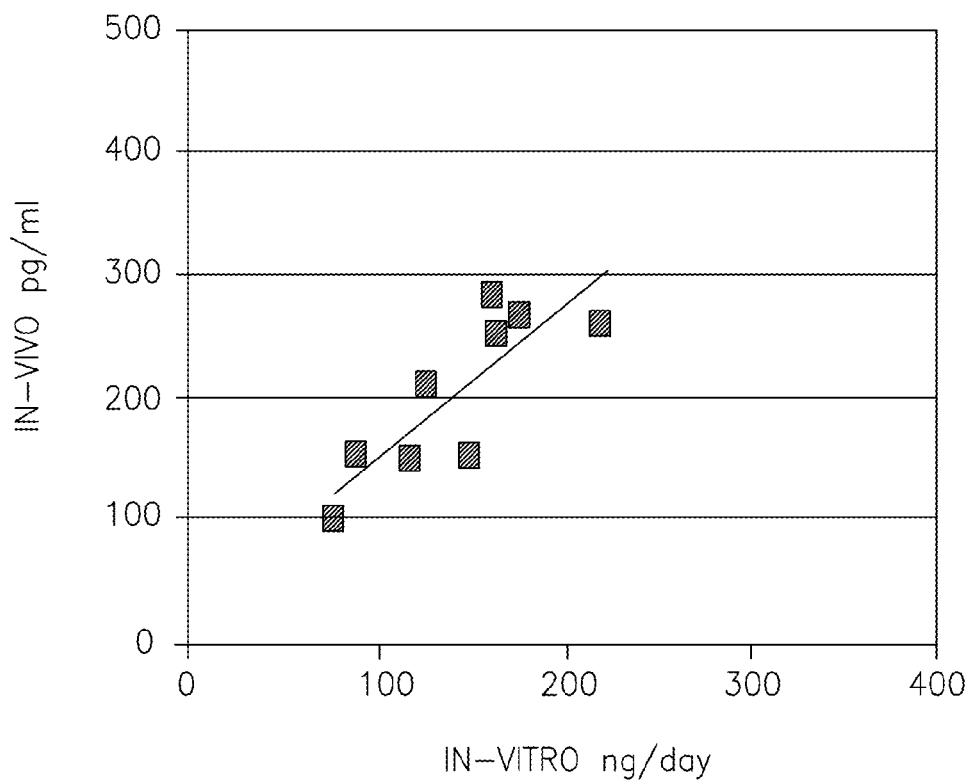
FIGS. 2A and 2B show, respectively, a correlation analysis between in-vitro secretion of pre-implanted mIFNα-TMOs and hEPO-TMOs and the serum in-vivo levels following their implantation, in accordance with an embodiment of the invention.
Figure 2B:
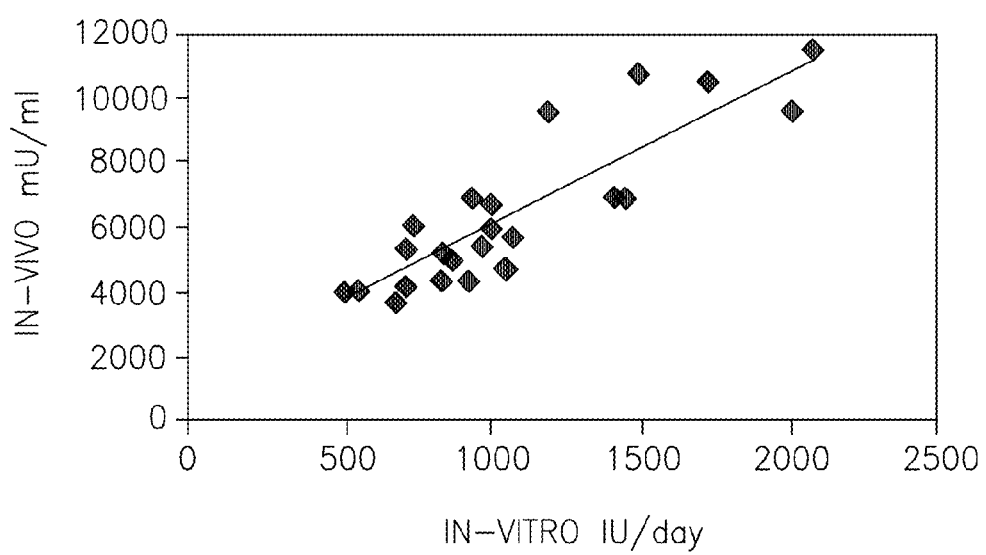

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

In the following detailed description, numerous specific details are set forth in order to provide a thorough understanding of the present invention. However, it will be understood by those skilled in the art that the present invention may be practiced without these specific details.

Exemplary Definitions of Terms Used Herein

The term "explant" as used herein, refers in some embodiments of the invention, to a removed section of living tissue or organ from one or more tissues or organs of a subject.

The term "dermal micro-organ" or "DMO" as used herein, refers in some embodiments of the invention, to an isolated tissue or organ structure derived from or identical to an explant that has been prepared in a manner conducive to cell viability and function, while maintaining at least some in vivo interactions similar to the tissues or organ from which it is obtained. Dermal micro-organs may include plurality of dermal components that retain the micro-architecture of the tissue or organ from which they were derived, and three dimensional structure of the dermal tissue from which they are derived, having dimensions selected so as to allow passive diffusion of adequate nutrients and gases to cells within the MO and diffusion of cellular waste out of the cells of the MO so as to minimize cellular toxicity and concomitant death due to insufficient nutrition and accumulation of waste. Dermal micro-organs may consist essentially of a plurality of dermis components (tissue components of the skin located below the epidermis). These components may contain skin fibroblast, epithelial cells, other cell types, bases of hair follicles, nerve endings, sweat and sebaceous glands, and blood and lymph vessels. Wherever used herein below, the description of the embodiments related to MO relates also to dermal MO whenever the term "dermal tissue" is used, it also relates to "dermal organ".

As used herein, the term "microarchitecture" refers, in some embodiments of the invention, to the characteristic of the explant in which, in one embodiment at least about 50%, in another embodiment, at least about 60%, in another embodiment at least about 70%, in another embodiment, at least about 80%, and in another embodiment, at least about 90% or more of the cells of the population, maintain, in vitro, their physical and/or functional contact with at least one cell or non-cellular substance with which they were in physical and/or functional contact in vivo. Preferably, the cells of the explant maintain at least one biological activity of the organ or tissue from which they are isolated.

The term "donor" as used herein, refers in some embodiments of the invention to a subject, from which the explant is removed and used to form, or which is already in the form of, one or more micro-organs.

The term "therapeutic micro-organ (TMO)" as used herein, refers in some embodiments of the invention to a micro-organ (MO) that can be used to facilitate a therapeutic objective, such as, for example, an MO that has been genetically altered or modified to produce a therapeutic agent, such as a protein or and RNA molecule. The therapeutic agent may or may not be a naturally occurring body substance. Wherever used hereinbelow, the description of the embodiments related to TMO relates also to DTMO which is a therapeutic Dermal MO which may be in some embodiments of the invention genetically modified.

The term "implantation" as used herein, refers in some embodiments of the invention, to introduction of one or more TMOs or DTMOs into a recipient, wherein said TMOs or DTMOs may be derived from tissues of the recipient or from tissues of another individual or animal. The TMOs or DTMOs can be implanted in a slit within the skin, by subcutaneous implantation, or by placement at other desired sites within the recipient body.

The term "recipient" as used herein refers, in some embodiments of the invention, to a subject, into which one or more TMOs or DTMOs are implanted.

The term "clamping" (e.g., the skin) as used herein may refer to any similar action or any action with a similar purpose, for example, "pinching" (e.g., the skin).

The term "in vitro" as used herein should be understood to include "ex-vivo".

The term "coring tube" as used herein may relate, individually or collectively, to the terms "cutting tool", "cutting tube" and "coring needle", as well as to any other elements with similar functionalities.

While, for clarity and completeness of presentation, all aspects of the production and utilization of DTMOs are described in this document, and embodiments of the invention are described from the start of the processes to their ends, it should be understood that each of the aspects described herein can be used with other methodologies and/or equipment for the carrying out of other aspects and can be used for other purposes, some of which are described herein. The present invention includes portions devoted to the preparation and maintenance of dermal micro-organs for transformation into DTMOs. It should be understood that the dermal micro-organs produced according to these aspects of the invention can be used for purposes other than for transformation into DTMOs In some embodiments of the invention, the micro-organ is a dermal micro-organ including a plurality of dermis components, for example, fibroblasts and/or epithelial components containing nerve endings and/or sweat glands and/or sebaceous glands and/or blood and lymph vessels and/or elastin fibers and/or collagen fibers and/or endothelial components and/or immune system derived cells and/or extra-cellular matrix. As shown by the test results summarized in the Examples section below (Example 5, FIG. 8), conventional subcutaneous implantation of a micro-organ including epidermal layers ("split thickness skin MO") in mice and pigs (data in pigs is not shown), may result in formation of keratin cysts or macro-keratin cysts. In contrast, when skin tissue is sampled to obtain a DMO according to exemplary embodiments of the invention, no cysts or macro cysts are observed in mice, pigs or in humans. It should be noted that the biological activity (for example, secretion of a therapeutic protein, e.g., erythropoietin and elevation of hematocrit as a result) of a DTMO according to embodiments of the invention may be comparable to or even higher than split thickness skin derived TMO (see Example 4). Namely, both types of preparation may release the same amount of erythropoietin; however, the DTMO may produce and secrete higher protein levels per unit than those of split thickness derived TMO.

In general, production of DTMOs may include DMO harvesting, maintaining the DMO and/or modifying the DMO and/or genetically altering them and, in some embodiments, verifying the production of a desired agent (for example proteins) by the DMO. Utilization of the DTMO may include production, within a patient's or animal's own body, of therapeutic substance, such as proteins, for treatment of a subject. For example, the DTMO can be implanted into or under the skin or within the body of the subject to produce the agent/protein in vivo. In the case of tissue from another subject, the implant is optionally protected from reaction by the recipient's immune system, for example, by housing the DTMO in an immunoprotective capsule or sheath. For example, a membrane can be positioned to surround the DTMO, either by placing the DTMO in a capsule prior to implantation or otherwise. The membrane should have a pore size that is sufficiently large to allow for the passage of nutrients, waste and the therapeutic agent yet sufficiently small to prevent passage of cells of the immune system.

In some embodiments of the invention, the dermal micro-organ may contain tissue of a basal epidermal layer and, optionally, other epidermal layers of the skin. In other embodiments, the dermal micro-organ does not include basal layer tissue.

In some embodiments of the invention, the DMO does not include epidermal layers. In other embodiments, the DMO may contain a few layers of epidermal tissue.

In one embodiment of the invention, the DMO includes the entire cross-section of the dermis. In another embodiment of the invention, the dermal micro-organ includes part of the cross-section of the dermis. In a further embodiment, the DMO includes most of the cross section of the dermis, namely, most of the layers and components of the dermis including the papillary and reticular dermis. In a further embodiment, the DMO includes primarily dermal tissue, but may also include fat tissue. In some embodiments of the invention, the DMO does not produce keratin or produces a negligible amount of keratin, thereby preventing the formation of keratin cysts following subcutaneous implantation in a recipient.

The DMO to be harvested can be removed from the body by any means of removing tissue known in the art, such as biopsy procedures. The harvesting procedure keeps intact the micro-architecture of the tissue from which it is removed. In one embodiment the DMO may be obtained by direct biopsy and be then cut to the required size or have non-desired tissue cut from it. In another embodiment, a tissue sample may be obtained by direct biopsy, in which the desired size of the dermal micro-organ is obtained and no further processing is required.

In some embodiments of the invention, the dermal micro-organ is directly harvested from the body, and the dimensions of a cutting tool used to harvest the dermal micro-organ may be, for example, about 1-4 mm in diameter. In another embodiment, the dimension may be, for example, 1.71 mm in diameter. In another embodiment the dimension may be, for example, 1-3 mm in diameter. In another embodiment, the dimension may be, for example, 2-4 mm in diameter. In another embodiment the dimension may be, for example, 1-2 mm in diameter. In another embodiment the dimension may be, for example, about 1.5 mm in diameter. In another embodiment, the dimension may be, for example, about 2 mm in diameter. In some embodiments, the harvested dermal micro-organ may not retain its cylindrical shape after harvesting, i.e., at least one dimension of its cross section may expand while at least another dimension of its cross section may contract. In one embodiment, for example, at least one dimension may be 0.5-3.5 mm and at least one dimension may be 1.5-10 mm.

In another embodiment, the dimensions of the tissue being harvested may be, for example, about 5-100 mm in length. In another embodiment, the dimensions of the tissue being harvested may be, for example, about 10-60 mm in length. In another embodiment, the dimensions of the tissue being harvested may be, for example, about 20-60 mm in length. In another embodiment, the dimensions of the tissue being harvested may be, for example, about 20-50 mm in length. In another embodiment, the dimensions of the tissue being harvested may be, for example, about 20-40 mm in length. In another embodiment, the dimensions of the tissue being harvested may be, for example, about 20-100 mm in length. In another embodiment, the dimensions of the tissue being harvested may be, for example, about 30-100 mm in length. In another embodiment, the dimensions of the tissue being harvested may be, for example, about 40-100 mm in length. In another embodiment, the dimensions of the tissue being harvested may be, for example, about 50-100 mm in length. In another embodiment, the dimensions of the tissue being harvested may be, for example, about 60-100 mm in length. In another embodiment, the dimensions of the tissue being harvested may be, for example, about 70-100 mm in length. In another embodiment, the dimensions of the tissue being harvested may be, for example, about 80-100 mm in length. In another embodiment, the dimensions of the tissue being harvested may be, for example, about 90-100 mm with an aspect of some embodiments of the invention, a closed, sterile, bioreactor apparatus may be used to carry, support and/or alter the DMO or DTMO throughout a harvesting, mm in length. In another embodiment the length may be around 20 mm. In another embodiment, the length may be about 30 mm. In another embodiment, the length may be about 40 mm.

When a dermal MO has the above listed dimensions, it maybe maintained in vitro, e.g., in a growth medium under proper tissue culture conditions for extended periods of time, for example, several days, several weeks or several months. The DMO may be maintained, for example, in-vitro in defined growth media. In one exemplary embodiment the growth media may include growth factors, fetal calf serum (FCS), or human serum, e.g., Synthetic Serum Substitute (SSS). In another exemplary embodiment the growth media may include serum either from the donor or the recipient subject. In yet another embodiment the growth media may include autologous serum.

In accordance with an aspect of some embodiments of the invention, a closed, sterile, bioreactor apparatus may be used to carry, support and/or alter the DMO or DTMO throughout a harvesting, alteration and implantation process, e.g., from harvesting to implantation, as described in detail below, e.g., with reference to FIG. 22. According to some exemplary embodiments, at least part of the bioreactor apparatus may be formed of disposable material.

In accordance with an aspect of some embodiments of the invention, the bioreactor apparatus may be loaded into a docking station, which may be used to carry out various processes and/or to maintain the DMO/DTMO under desired conditions. The apparatus may be optionally computer controlled according to a protocol.

In accordance with an aspect of some embodiments of the invention, only a portion of the DTMO generated may be used in a given treatment session. The remaining DTMO tissue may be returned for maintenance and/or may be stored (e.g., cryogenically or otherwise) for later use.

It is a feature of some embodiments of the invention that a large number of dermal micro-organs may be processed together in a batch process into DTMOs, as described below. This may allow for more convenient processing, but will not allow for determination of the secretion level of each DTMO separately.

In some exemplary embodiments of the invention a potency assay may be performed for the therapeutic agent, which may be produced and/or secreted by either a single DTMO or a batch of DTMOs. The potency assay may include, for example, a cell proliferation assay in which the proliferation response of the cells is mainly dependent on the presence of the therapeutic agent in the growth media of the cells.

The term "skin-related tissue structure", as used herein, refers to a structure of tissue components that may be stabilized and/or supported by apparatuses defined herein to enable the harvesting of a dermal micro-organ therefrom. A skin-related tissue structure may include components of the epidermal tissue, and components of the dermal tissue. Optionally, the skin-related tissue structure may include fat tissue and/or muscle tissue in the vicinity of the dermal tissue.

According to some embodiments of the invention, a method of harvesting the dermal micro-organ may include stabilizing and supporting a skin-related tissue structure from which a dermal micro-organ is to be harvested, e.g., such that at least the dermal micro-organ and/or one or more other tissue segments in its vicinity are maintained at a desired shape and/or position, separating at least a portion of the dermal micro-organ from surrounding tissue, and extracting the separated dermal micro-organ, as described in detail below.

FIG. 1 shows an overview of a methodology 200 for producing and utilizing DMOs and DTMOs, in block diagram form, in accordance with an exemplary embodiment of the invention. At block 202 a DMO is harvested from a subject. In some embodiments of the invention, the DMO is harvested from the same subject to which therapy will later be applied. In an embodiment of the invention, the DMO is from dermal tissue. Optionally, other tissues are harvested and used in a manner similar to that described below with reference to dermal tissue. While the method described below is exemplary, other methods of harvesting tissue samples can be used in some embodiments of the invention. If desired, the DMO can be cryogenically stored for later use (i.e., introduction at the same stage of the process). Alternatively, for certain embodiments, the DMO can be implanted directly back into the patient from which it was harvested to produce a therapeutic, cosmetic, or other physiological affect.

In order for a DMO to be a viable micro-organ, it must have at least one dimension that is small enough that nutrients can diffuse to all the cells of the DMO from a nutrient medium which contacts the DMO and that waste products can diffuse out of the DMO and into the medium. This enables the DMO to be viable in vitro long enough for the further processing described below and for the optional further utilization of the DMO as a source for a therapeutic agent, such as a protein. The method of harvesting a DMO as described above, generally results in a DMO having an in vitro life of several months.

After the DMO is harvested; it is optionally visually inspected to determine that it is properly formed and that it has the desired dimensions. Inspection can also be performed optically. It is then optionally mounted on a holder and transported (block 206) to an apparatus (the bioreactor, as will be described below) in which it can be genetically altered. A suitable genetic modification agent is prepared (block 208). Alternative exemplary methods of preparing the agent include creation of aliquots with a desired amount, using a predefined dilution buffer of modifying agent such as for example a viral vector, possible cryogenic storage and thawing of the modifying agent, under controlled temperature (0-4.degree. C.), and validating the activity of the modifying agent. All of these processes are well known in the art. At this point the DMO can be stored cryogenically, for later introduction at the same place in the process. This can be performed using known protocols for gradual freezing of tissues and cells, using for example, DMEM medium containing 10% DMSO.

At block 210 the DMO is genetically altered. As described above, many methods of genetic alteration are known and may be used in conjunction with the present invention. As an example, the following description is based on using a viral vector to insert a gene into the cells of the DMO. This process is well known and will not be further described, except as to the particular methodology and apparatus for introducing the virus to the DMO.

At block 212 the genetically altered DTMO is optionally tested for production and secretion rates of the therapeutic agent. There are various methods of determining the quantity of secretion, for example, ELISA, other immunoassays, spectral analysis, etc. In addition the quality of the secretion is optionally tested, for example for sterility and activity of the secreted protein. This may be performed periodically or continuously on-line. At this point the DTMO can be cryogenically stored for later use.

At blocks 214 and 216, the amount of DTMO required for producing a desired therapeutic effect is determined. As indicated below, the therapeutic dose requirements can be estimated from measured secretion rates, patient parameters and population statistics on the estimated or known relationship between in vitro secretion and in vivo serum levels.

At block 218 the selected number of the DTMOs are loaded into implantation tools. Exemplary implementation tools have been described above. If needed, for allografts or xenografts or for other reasons, the DTMO can be encapsulated. If the DTMO must be transported prior to being transported to the implantation tools, it is optionally held (220) in a maintenance station, in which the temperature, humidity, etc. are held at levels that allow the DTMO to stay viable during transport. The remaining DTMO material is optionally maintained in vitro for future use. This can be at warm incubator conditions (30-37.degree. C.), in conditions as described above or at cool incubator conditions (4.degree. C.), which may prolong its viability in vitro.

Figure 7:
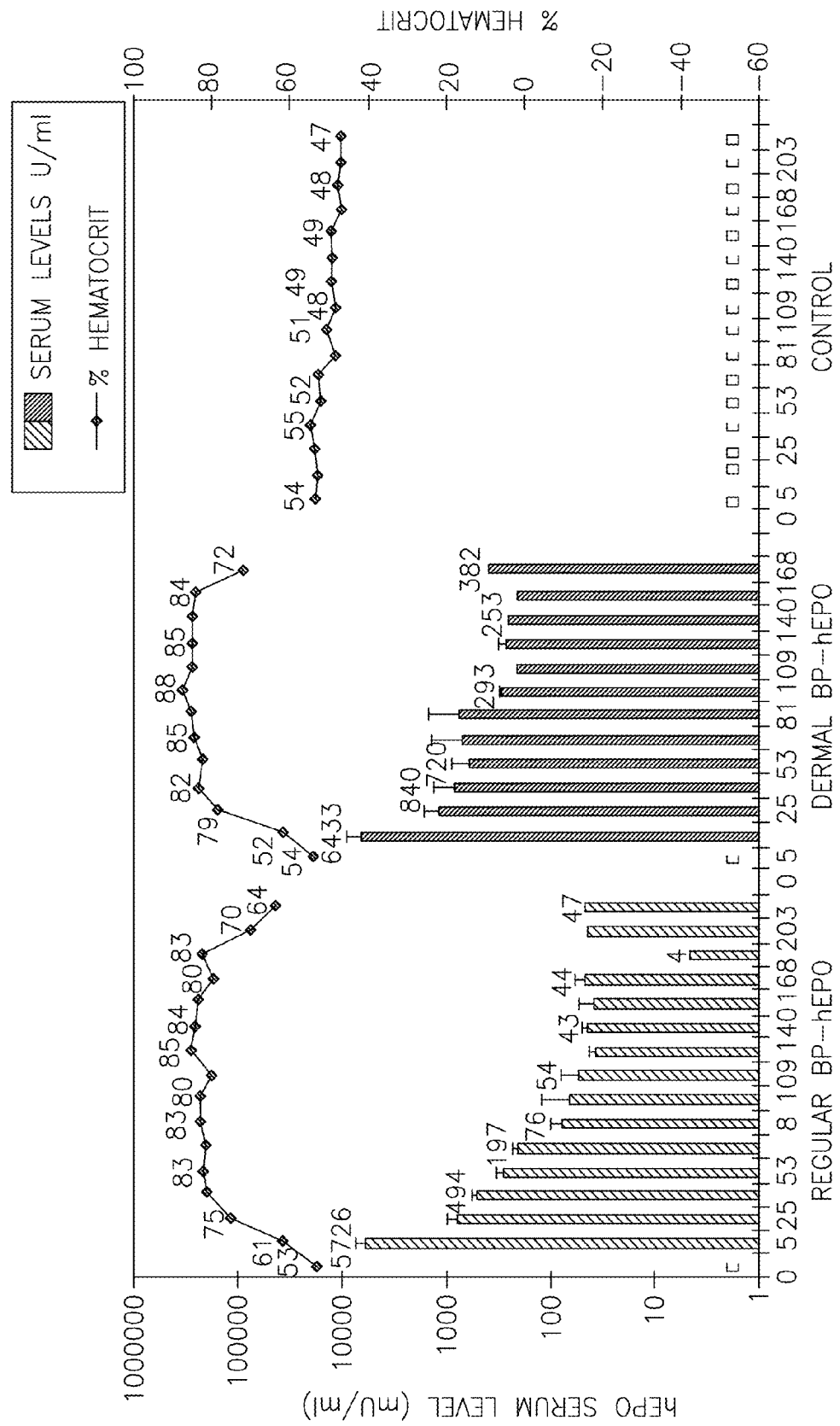
FIG. 7 demonstrates in vivo hEPO serum levels and physiological effect on hematocrit levels following subcutaneous implantation of DTMO-hEPO and split thickness skin TMO-hEPO in SCID mice.

At block 224, a subset of the DTMOs is implanted into the subject. An exemplary embodiment of a method of implantation is described above. Other methods of doing so will occur to persons of skill in the art and are primarily dependent on the specific geometry of the micro-organ being used. Animal studies have shown that the DMOs and DTMOs remain viable in vivo, in the sense that the DTMO continues to produce and secrete the therapeutic agent for a period of weeks and months following implantation (FIG. 7). In animal studies, therapeutic amounts are produced for periods up to 160 days (or longer). While the tissue of the DMO or DTMO appears to be integrated or well taken into the tissue of the subject into which it is implanted (especially if the tissue is implanted in a tissue of the same kind from which it was harvested), the cells including the DMO or the DTMO continue to produce and secrete the therapeutic agent.

In either case, the in vivo performance of the DTMO is optionally determined (block 228). Based on this evaluation for example, and/or on past patient data (block 226), patient dosage may then be adjusted (block 230) by increasing the amount of the implant or removing some of the implant, as described below. As the efficacy of the implant changes, additional DTMO can be implanted.

Genetic alteration may generally include genetically engineering a selected gene or genes into cells that causes the cells to produce and optionally to secrete a desired therapeutic agent such as a protein. In an embodiment of the invention, at least part of the process of sustaining the DMO during the genetic alteration, as well as the genetic alteration itself, may be performed in a bioreactor, as described below.

Figure 10:
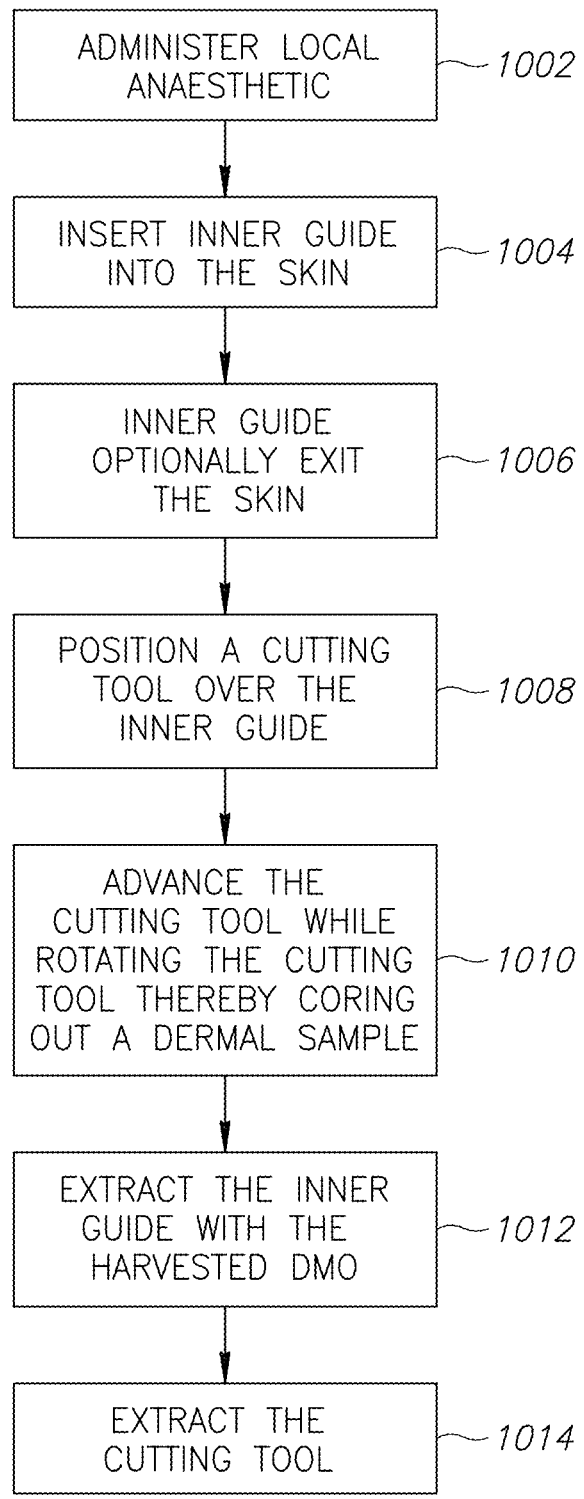
FIG. 10 is a schematic flowchart illustrating a method of harvesting a DMO according to some exemplary embodiments of the invention.
Figure 11:
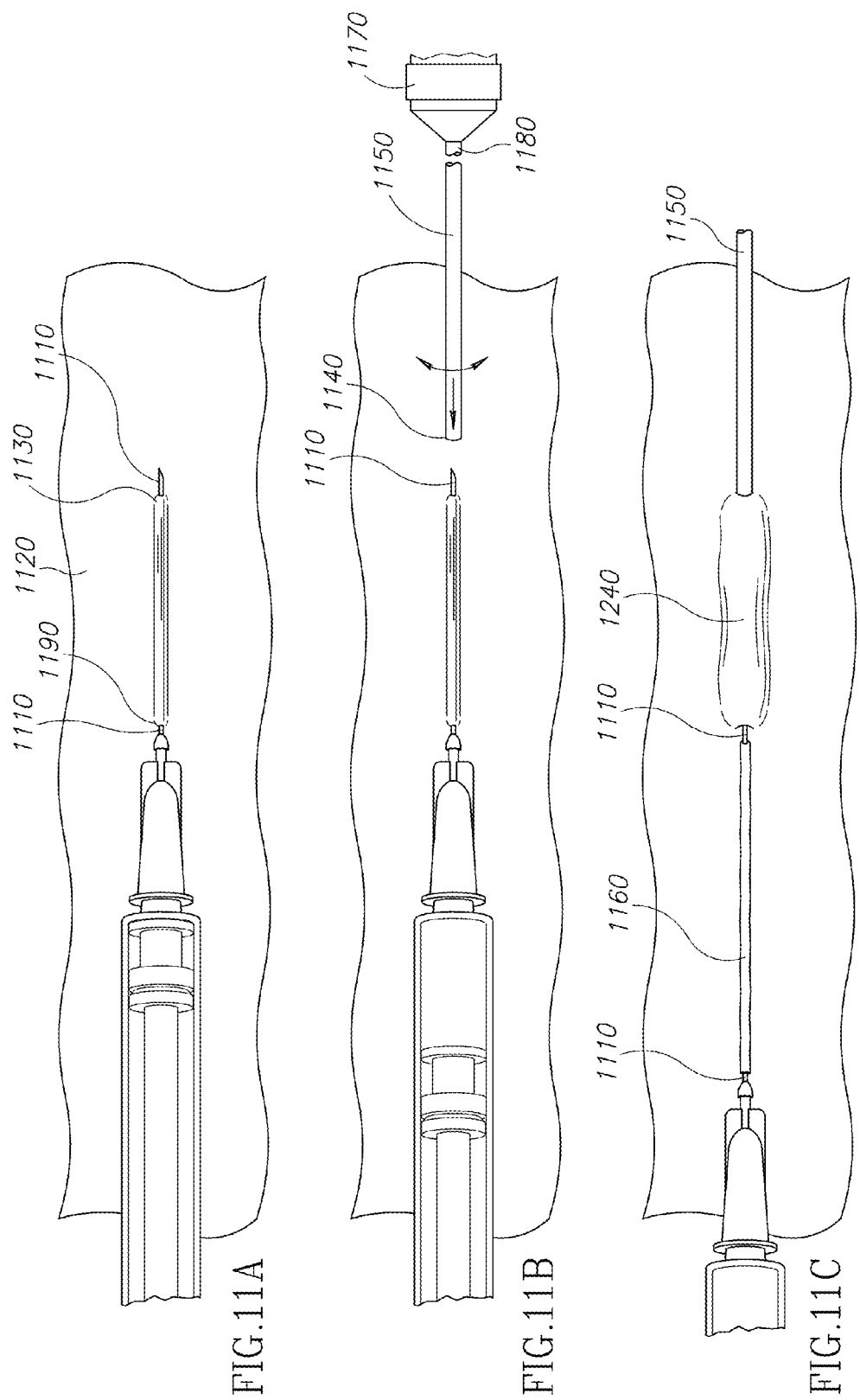
FIGS. 11a-11c are schematic illustrations of exemplary stages of harvesting a DMO in accordance with the method of FIG. 10.

Reference is now made to FIG. 10, which schematically illustrates a flowchart of a method of harvesting a dermal micro-organ according to some exemplary embodiments of the invention, and to FIGS. 11a-11c, which schematically illustrate exemplary stages of harvesting a dermal micro-organ 1160 located under a skin tissue portion 1120 in accordance with the method of FIG. 10.

As indicated at block 1002, the method may optionally include locally administering an anesthetic, e.g., as is known in the art, to the vicinity of the DMO to be harvested.

As indicated at block 1004, the method may further include inserting an inner guide 1110 into tissue portion 1120. Thin incisions ("lance cuts") 1190 and 1130 may be formed in the outer skin, preferably using a surgical lance, scalpel, or other sharp probe, in order to allow easier insertion of inner guide 1110, and also to prevent or minimize the harvesting of epidermal tissue. Inner guide 1110 may be inserted into portion 1120 via incision 1190, e.g., generally parallel to the skin surface and/or at a desired depth within the dermis or just under the skin. Inner guide 1110 may include a thin needle, rod, or any other suitable thin, generally straight, object able to be placed inside the dermis or in a subcutaneous space. For example, inner guide 1110 may include a needle of size 20-25 G, for example, about 22 G, as is known in the art. Inner guide 1110 may be inserted into the dermis or subcutaneous space and/or pushed generally horizontally, i.e., generally in parallel with the skin surface. The length of penetration of guide 1110 within the dermis may generally correspond to the length of the DMO to be harvested. For example, inner guide 1110 may be inserted manually, and hand guided within the dermis at a desired depth, which depth may be maintained substantially uniformly throughout the insertion process. Alternatively, inner guide 1110 may be inserted into and along the subcutaneous space, by manually sensing the boundary between the fibrous dermis and an underlying smooth fatty layer as the inner guide is inserted.

As indicated at block 1006, the method may optionally include guiding inner guide 1110 to exit the skin, e.g., at incision 1130. According to some exemplary embodiments, the distance between incisions 1190 and 1130 may be approximately equal to or larger than a required length of the DMO to be harvested.

As indicated at block 1008, the method may also include inserting a tubular cutting tool coaxially with and around inner guide 1110, such that the DMO may be trapped, i.e., positioned, between the inner guide 1110 and the cutting tool. This may be achieved, for example, by using a tubular cutting tool having an inner diameter larger than the outer diameter of inner guide 1110. The cutting tool may include any suitable cutting tool, for example, a coring tube 1150. Coring tube 1150 may include a generally symmetrically sharpened tubular tool, e.g., a hypo tube processed to have sharpened cutting edge with a desired shape. Coring tube 1150 may include, for example, a standard medical grade tube, having a thin wall, e.g., having a thickness of between 0.05 mm and 0.3 mm Coring tube 1150 may have a diameter, for example, between 1 mm and 10 mm. The dimensions, e.g., the diameter, of coring tube 1150 and/or the dimensions of inner guide 1110 may be predetermined based on the volume and/or dimensions of the DMO intended to be harvested. Coring tube 1150 may have a sharpened end ("tip") 1140 adapted to serve as a cutting edge. Coring tube 1150 may be inserted through tissue portion 1120, preferably after creating initial incisions, E.G., INCISION 1130, on the outer surface of the skin in order to prevent harvesting of epidermal tissue.

According to one exemplary embodiment of the invention, e.g., as illustrated in FIG. 11b, the method may include initially positioning end 1140 of coring tube 1150 over a distal end of inner guide 1110, e.g., at incision 1130, and sliding coring tube 1150 along the length of inner guide 1110, e.g., towards incision 1190, to harvest the dermal DMO.

As indicated at block 1010, in one embodiment the method may include rotating the cutting tool while advancing the cutting tool, e.g., towards the proximal end of the inner guide. For example, a medical drill or other suitable tool or rotation mechanism may be used to rotate coring tube 1150 while it is advanced manually or automatically, thereby more smoothly harvesting DMO 1160. For example, a proximal end 1180 of coring tube 1150 may be connected to a medical drill 1170, such as, for example, the Aesculap Micro Speed drill manufactured by Aesculap AG & Co. KG, Am Aesculap Platz, D-78532 Tuttlingen, Germany, which may include a control unit, a motor, a connection cord, a hand piece and/or a foot switch, catalogue numbers GD650, GD658, GB661, GB166 and GB660, respectively. Such a drill, or any other suitable drill or rotation mechanism, may be used to rotate the cutting edge of the cutting tool at a rotational speed appropriate for cutting of the dermal tissue, for example, a relatively high rotational speed, for example, a speed higher than 1,000 RPM, e.g., between 1,000 RPM and 10,000 RPM. For example, tube 1150 may be rotated at a rotational speed higher than 2,000 RPM, e.g., approximately 7,000 RPM. Alternatively, a relatively low rotational speed of less than 1000 RPM may be used, or no rotation at all, as described below. Optionally, the rotational speed of the drill may vary in an oscillatory manner, i.e., the direction of rotation may vary periodically between "clockwise" and "counterclockwise" directions. While rotated by drill 1170, coring tube 1150 may be manually or automatically advanced, e.g., towards the proximal end of inner guide 1110, e.g., towards incision 1190. The method may also include stopping the forward motion of coring tube 1150, for example, when tip 1140 has been advanced just beyond incision 1190. According to some exemplary embodiments of the invention, at least part of an inner surface and/or an outer surface of tube 1150 may be coated with a low friction material, e.g., Teflon, Parylene or any other suitable coating material, e.g., to ease the separation of the harvested tissue from the inner surface of the cutting tool in a subsequent action and/or to reduce any forces acting on the tissue during the cutting action, as described below.

In another embodiment, a fast-acting, e.g., spring-loaded, insertion mechanism may be used to assist coring tube 1150 in penetrating the harvesting target and cutting the dermis, e.g., with substantially no rotational motion of the coring tube.

As indicated at block 1012, the method may include withdrawing inner guide 1110, e.g., having DMO 1160 impaled thereon, from within coring tube 1150, thereby to extract DMO 1160 from portion 1120.

According to some embodiments, DMO 1160 may be left impaled on inner guide 1110. In such a case, inner guide 1110 may be used to handle, transport, and/or manipulate the DMO 1160. Alternatively DMO 1160 may be, for example, carefully removed from inner guide 1160 into a bioreactor processing chamber, e.g., as described in detail below with reference to FIG. 22, or onto various transfer devices (not shown) adapted for transferring the DMO to a different mount or into a chamber for further processing. Such transfer devices may include, for example, forceps, vacuum grippers or any other mechanical devices able to grip DMO 1160 and/or push DMO 1160 off inner guide 1110. In addition, suitable fluids, such as sterile fluids, may be used, either alone or in conjunction with the means listed above, to assist in removing the DMO from inner guide 1160.

As indicated at block 1014, the method may also include withdrawing the cutting tool, e.g., coring tube 1150, from skin portion 1120.

It will be appreciated by those skilled in the art that any combination of the above actions may be implemented to perform harvesting according to embodiments of the invention. Further, other actions or series of actions may be used.

According to some embodiments of the invention, the harvesting method may additionally include externally stabilizing and/or supporting the DMO to be harvested and/or tissue in the vicinity of the DMO to be harvested e.g., using an external support device and/or mechanism, for example, in addition to internally stabilizing and/or supporting the dermis, e.g., by the inner guide, as described below.

Figure 12:
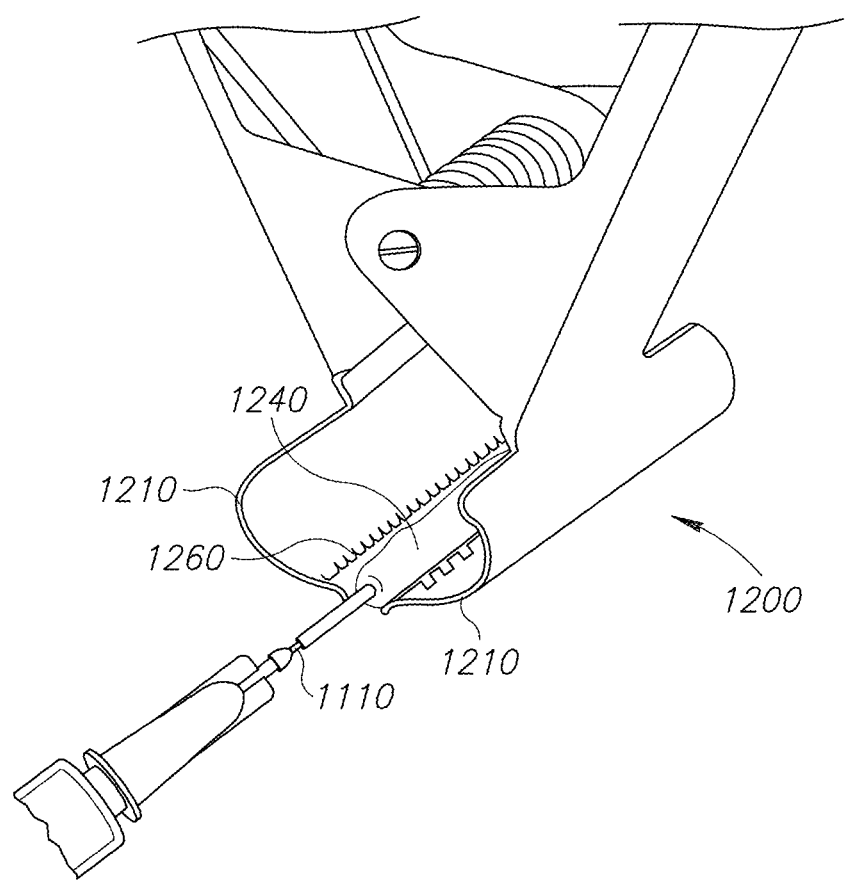
FIG. 12 is a schematic illustration of a clamping tool that may be used by a dermal harvesting apparatus in accordance with some exemplary embodiments of the invention.

Reference is also made to FIG. 12, which schematically illustrates a stabilizing clamping tool 1200, which may be used in conjunction with a dermal harvesting apparatus in accordance with some exemplary embodiments of the invention.

According to exemplary embodiments of the invention, tool 1200 may include a clamping mechanism having clamping edges 1210. For example, tool 1200 may include a pinching clamp or forceps, e.g., as are known in the art. Tool 1200 may include a spring clamp having a constant clamping force, or a controllably variable clamping force. Tool 1200 may be placed on the skin surface parallel to and on either side of inner guide 1110, e.g., such that when closed, clamping edges 1210 may be positioned beneath inner guide 1110. Clamping edges 1210, when brought close together, may function to stabilize and/or support inner guide 1110 and/or a skin portion 1240 associated with the DMO to be harvested, such that the DMO may be stabilized while being cut by tube 1150. Coring tube 1150, in this case, may be pushed through clamping edges 1210 concentric or non-concentric to inner guide 1110, while force is applied. According to some exemplary embodiments of the invention, clamping edges 1210 may include at least one or two rows of serrated teeth 1260 in order to provide improved clamping of portion 1240 and reduce, e.g., minimize, lateral movement of the skin during the coring process.

Other tools and/or mechanisms may be used to apply force to the outer skin in order to cause similar compression of the dermis surrounding the inner guide. Alternatively, other devices and/or methods for stabilizing the dermis to be harvested may be used, such as twisting the inner guide and holding it at a substantially fixed position with respect to the rotation of the coring tube.

Figure 13:
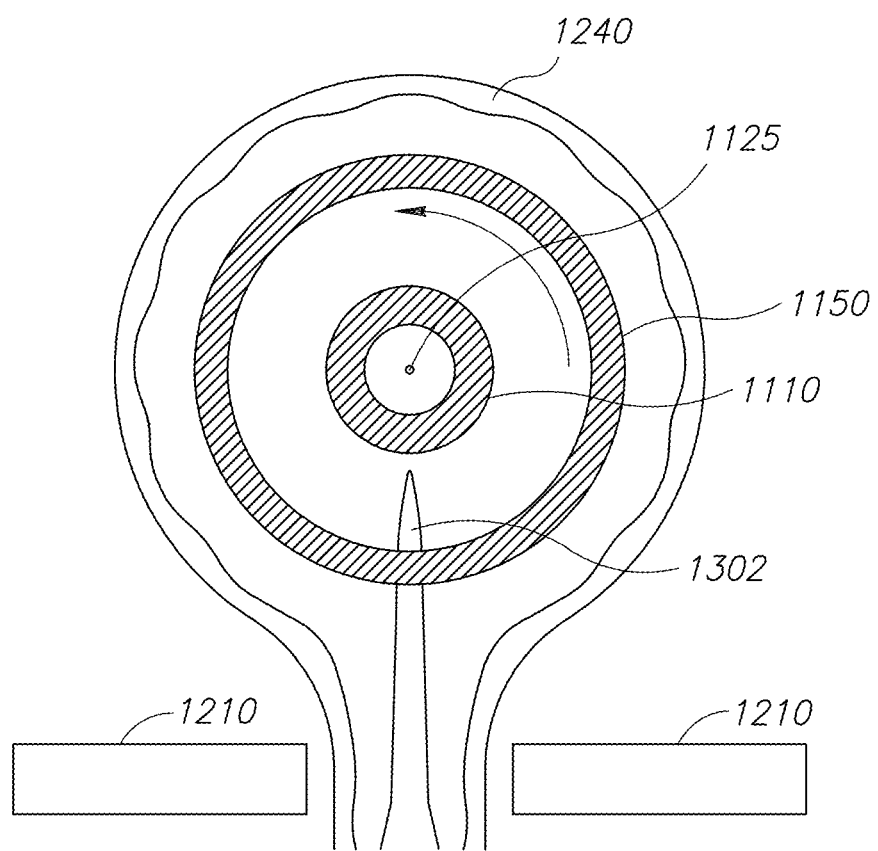
FIG. 13 is a schematic illustration of a dermal harvesting apparatus including a coring tube inserted into source tissue for a DMO, and harvesting coaxially with an inner guide needle in accordance with some exemplary embodiments of the invention.

Reference is also made to FIG. 13, which schematically illustrates a cross sectional view of coring tube 1150 inserted coaxially over and along inner guide 1110 in accordance with some exemplary embodiments of the invention.

According to some embodiments of the present invention, inner guide 1110 may be placed in skin portion 1120 at a position such that an axis 1125 of guide 1110 is positioned substantially at the center of DMO 1160. In such a case, coring tube 1150 may be substantially coaxially aligned with inner guide 1110, such that DMO 1160 is impaled on inner guide 1110 in an approximately symmetrical manner.

However, according to other exemplary embodiments of the invention, the inner guide and the coring tube may be positioned in any other suitable arrangement. For example, the inner guide may be positioned in the subcutaneous space, such that the desired DMO to be harvested may be primarily located above the inner guide and wrapped around it. Accordingly, the coring tube may be inserted over the inner guide and/or guided such that the inner guide is positioned close to or touches the lower inner surface of the coring tube as it cuts the DMO. In such a case, the inner guide may hold the DMO, which may rest, for example, along the upper surface of the inner guide when being removed.

According to some embodiments of the present invention, the above described manual procedures may be facilitated by an integrated apparatus (not shown) configured to perform some or all of the above procedures for harvesting the DMO. For example, in regard to one harvesting method embodiment, the integrated apparatus may be configured to enable positioning and guiding the insertion of inner guide 1110, attaching clamping tool 1200, guiding the insertion of coring tube 1150 and controlling its movement during the cutting process, and/or removing DMO 1160 being attached to inner guide 1110. Such an apparatus may enable relatively simple operation when performing a harvesting procedure.

According to some exemplary embodiments of the invention, a method of harvesting a DMO from a subject may include generating and/or maintaining a skin-related tissue structure associated with the DMO, e.g., located generally at a targeted harvest site for harvesting the DMO, at a desired shape and position such that the cutting tool may be able to separate at least part of the DMO from tissue in the vicinity of the DMO. For example, an epidermis portion in the vicinity of the targeted harvest site may be lifted, e.g., by attaching at least part of the epidermis portion to a predefined, e.g., substantially flat, surface area such that at least part of the skin-related tissue structure may be lifted and maintained at the desired shape and/or position. According to some exemplary embodiments, attaching the epidermis to the predefined surface may include applying a vacuum condition, e.g., as described below. Alternatively or additionally, attaching the epidermis to the predefined surface may include applying an adhesive to the surface.

Figures 14A, 14B:
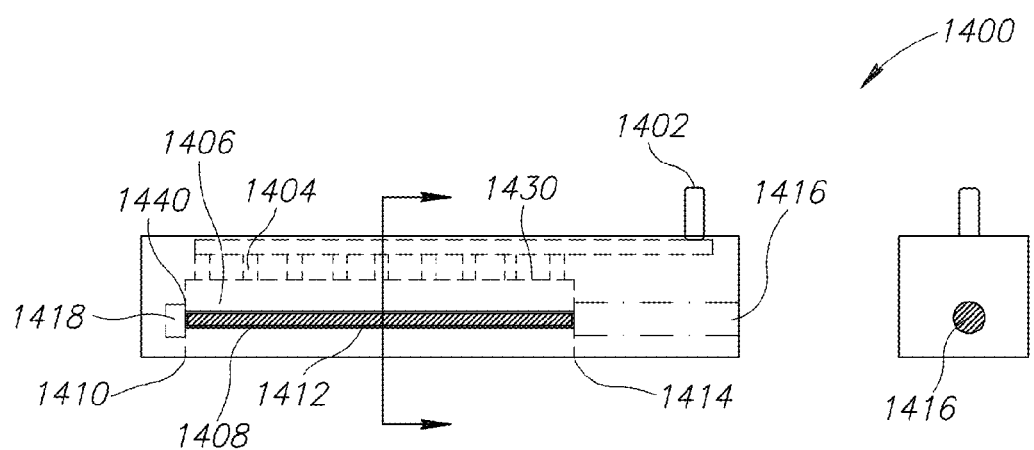
FIGS. 14a-14c are schematic illustrations of a front view, a side view, and top view, respectively, of a dermal vacuum harvesting apparatus according to an exemplary embodiment of the invention.
Figure 14C:
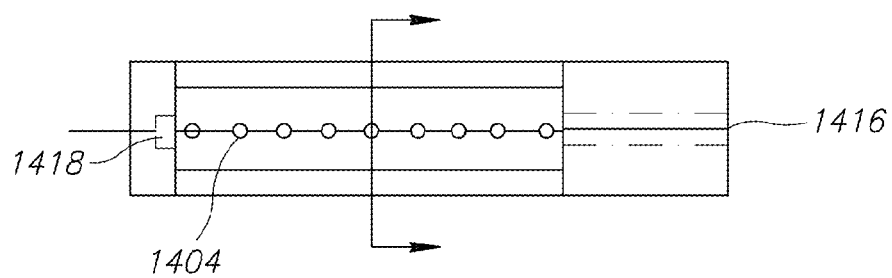
Figure 15:
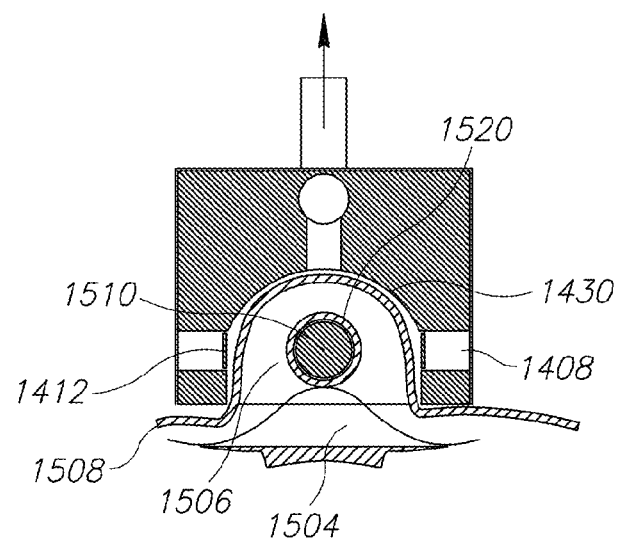
FIG. 15 is a schematic illustration of a cross-sectional side view of the apparatus of FIGS. 14a-14c supporting a dermal micro-organ at a desired position according to one exemplary embodiment of the invention.

Reference is now made to FIGS. 14a-14c, which schematically illustrate a front view, a side view, and a top view, respectively, of a dermal harvesting apparatus 1400 for harvesting a DMO according to one exemplary embodiment of the invention, and to FIG. 15, which schematically illustrates a cross-section side view of apparatus 1400 being implemented for externally supporting a skin-related tissue structure including DMO 1510 at a desired position according to one exemplary embodiment of the invention.

Apparatus 1400 may include a vacuum chamber, e.g., a generally cylindrical longitudinal chamber 1406, having a top support surface 1430 fluidically connected via a plurality of channels 1404 to a vacuum inlet 1402. Vacuum inlet 1402 may be fluidically connected to at least on vacuum source, e.g., a vacuum pump (not shown), to provide a vacuum condition to chamber 1406. Surface 1430 and/or channels 1404 may be configured to enable attaching to surface 1430 at least part of an epidermal layer 1508 associated with DMO 1510, e.g., located generally above DMO 1510, when a vacuum condition is applied to chamber 1406, e.g., by the vacuum source.

Apparatus 1400 may also include a guiding channel 1416 for guiding a cutting tool, e.g., a coring tube 1520, and maintaining the cutting tool at a predetermined location, e.g. a predetermined distance from upper surface 1430. For example, the upper surface of cutting tool 1520 may be located at a distance, for example, of approximately 1 mm from upper surface 1430. In other embodiment, other ranges, such as for example, 0.3-2.0 mm, may also be used. Channel 1416 may include, for example, a generally cylindrical channel having a diameter slightly larger than the outer diameter of coring tube 1520. Coring tube 1520 may include a coring needle having a size of, e.g., between 1 mm and 10 mm, for example, 14 G (corresponding to an outer diameter of approximately 2.11 mm) and having a symmetrically sharpened cutting edge.

According to exemplary embodiments of the invention, surface 1430 may be flat, generally curved, or may have any other suitable shape. For example, in one embodiment, surface 1430 may have a radius of curvature of about 3.5 mm. In one embodiment, chamber 1406 may have a width of, for example, about 4 mm. Furthermore, in some embodiments, chamber 1406 may have a height of, for example, about 5 mm. In other embodiments, other ranges, such as for example, 3-25 mm, may also be used for the radius of curvature of surface 1430 and/or the width and/or height of chamber 1406, for example, any desired dimensions in the range of 3-25 mm may be used in some embodiments of the invention. The length of chamber 1406 may be generally similar to the length of the DMO being harvested, for example, approximately 30 mm in length; however, other ranges, for example, in the range of 5-100 mm, may be used for the chamber length.

According to some exemplary embodiments, apparatus 1400 may include two channels 1408 located at least partially along two sides of chamber 1406, respectively, to allow clamping epidermis layer 1508, as described below. Channels 1408 may be positioned, e.g., centered, at a desired height, for example, at approximately the same height as where the center of the DMO is to be harvested. In one embodiment, the center of channels 1408 may be positioned at a height of about 2 mm below upper surface 1430. so that the clamping may stabilize and/or support the tissue being cut. According to these exemplary embodiments, apparatus 1400 may also include two flexible membrane elements 1412, on either the inner surface or outer surface of channels 1408, so as to allow external clamping of the tissue without substantially affecting the vacuum condition applied to chamber 1406. According to other embodiments of the invention, apparatus 1400 may not include elements 1412 and/or channels 1408.

According to exemplary embodiments of the invention, a method of harvesting DMO 1510 using apparatus 1400 may include forming two incisions (not shown), e.g., forming two lance cuts using a scalpel, in a skin portion associated with DMO 1510 at a predetermined distance, e.g., approximately 30 mm, which may correspond to the points at which coring tube 1520 is intended to enter and exit epidermis 1508 ("the entry and exit penetration sites"). The incisions may be formed in order to ensure that there will be substantially no epidermal component at the two ends of harvested DMO 1510, and/or to maintain a desired shape of the penetration sites such that they may heal efficiently, i.e., quickly and/or leaving relatively small scars. The method may also include placing apparatus 1400 in contact with epidermis layer 1508 ("the harvest site") such that the incisions are positioned underneath chamber 1406, i.e., in between points 1410 and 1414. The incisions may be positioned at points 1410 and/or 1414, respectively, or may be positioned between points 1410 and 1414 to help force the lance cuts to "open" once the vacuum condition is applied to chamber 1406. According to some exemplary embodiments, apparatus 1400 may optionally include a mechanism configured for creating the lance cuts, for example, spring loaded lancets that produce the lance cuts, e.g., after apparatus 1400 is placed on the harvest site and before the vacuum condition is applied to chamber 1406.

The method may also include inserting coring tube 1520 into channel 1416. Coring tube 1520 may be connected, for example, via a connector, e.g., a Jacobs Chuck or a friction holder, to a medical drill or any other suitable tool and/or mechanism, e.g., drill 1170 (FIG. 11), able to rotate coring tube 1520. Optionally, the rotational speed of the drill may vary in an oscillatory manner, i.e., the direction of rotation may vary periodically between "clockwise" and "counterclockwise" directions.

The method may also include applying a vacuum condition to chamber 1406, e.g., by activating the vacuum source. Consequently, the skin-related tissue structure may be drawn into chamber 1406 and epidermis 1508, e.g., between the lance cuts, may be firmly held against surface 1430. Epidermis 1508, dermis 1506, and/or fatty tissue components 1504 may additionally be drawn into chamber 1406, depending on the thickness of each of these tissue layers and the dimensions of chamber 1406. Thus, the dimensions of chamber 1406 may be designed in accordance with the anticipated thickness of one or more of the tissue layers and/or exterior clamping, e.g., as described herein, may be applied such that fat tissue 1504 drawn into vacuum chamber 1406 may be forced downwards and substantially out of chamber 1406.

The method may further include rotating coring tube 1520, e.g., using drill 1170 (FIG. 11) at a relatively high rotational speed, e.g., higher than 1,000 RPM, e.g., between 1,000 RPM and 10,000 RPM. For example, coring tube 1520 may be rotated at a rotational speed higher than 2,000 RPM, e.g., approximately 7,000 RPM. Alternatively, a relatively low rotational speed of less than 1000 RPM may be used, or no rotation at all, as described above. The method may also include advancing coring tube 1520 along vacuum chamber 1406, e.g., at least along the entire length of chamber 1406. Coring tube 1520 may be guided through channel 1416 in order to ensure that dermal micro-organ 1510 is harvested from approximately the same depth in the skin-related tissue structure along chamber 1406. Coring tube 1520 may be advanced manually, or using a motorized actuator (not shown), e.g., to control the speed at which coring tube 1520 may advance.

The method may also include detaching DMO 1510 from tissue surrounding DMO 1510. For example, apparatus 1400 may include an extension 1418, e.g., having a length of between 1 mm and 5 mm and a radius substantially equal to the radius of channel 1416, located substantially opposite channel 1416 such that coring tube 1520 may advance into extension 1418 after going through chamber 1406. Alternatively, a cutting surface 1440, e.g., formed of Silicone or other suitable material, may be positioned in extension 1418 such that the coring tube may, cut into surface 1440 to detach the harvested DMO. Additionally, a vacuum condition may be applied within coring tube 1520, e.g., from its back end, such that DMO 1510 may be actively drawn into coring tube 1520, thus urging final detachment of the DMO from the surrounding tissue.

The method may further include withdrawing coring tube 1520, including therein DMO 1510, from apparatus 1400.

Figure 16:
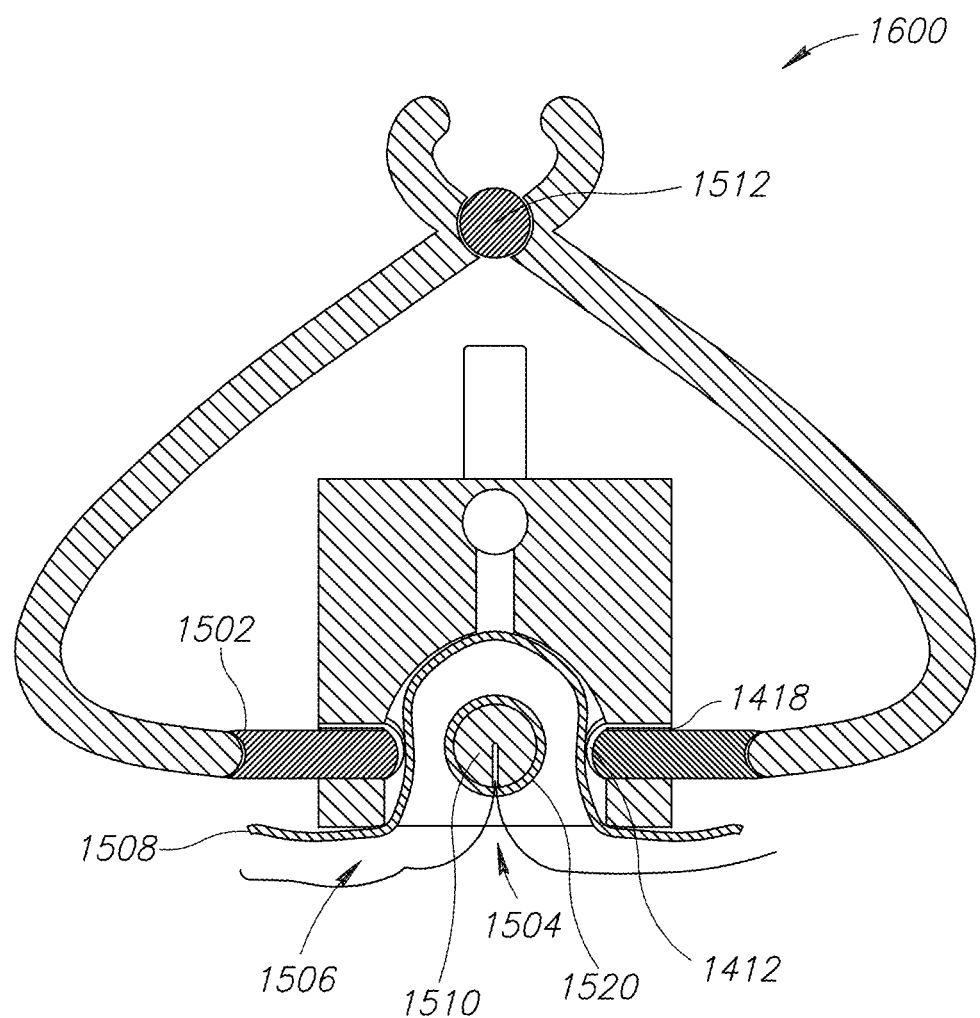
FIG. 16 is a schematic illustration of a cross-sectional view of the apparatus of FIG. 15 externally supporting a dermal micro-organ to be harvested at a desired position.

Reference is made to FIG. 16, which schematically illustrates a cross-sectional side view of apparatus 1400 being implemented for externally supporting a skin-related tissue structure at a desired position according to another exemplary embodiment of the invention.

According to the exemplary embodiment of FIG. 16, improved stabilization of dermis 1506 and/or improved prevention of recruitment of fat 1504 into vacuum chamber 1406 may be accomplished by external clamping of the skin-related tissue structure supported within the vacuum chamber. For example, a clamping tool 1600, e.g., analogous to the clamping tool described above with reference to FIG. 12, may be implemented to "pinch" the skin-related tissue structure supported inside vacuum chamber 1406, e.g., symmetrically. Two clamping ends 1502 of clamping tool 1600 may be inserted into channels 1408, respectively. Tool 1600 may be closed such that clamping ends 1502 may press down against flexible elements 1412. Thus, the skin-related tissue structure in chamber 1406 may be clamped from the sides without substantially affecting the vacuum condition in chamber 1406. A clamping force applied by clamping ends 1502 may correspond, for example, to a constant or variable force of a spring 1512 or other suitable device.

Although the above description may refer to a vacuum chamber having a generally constant shape and/or size along its longitudinal axis, it will be appreciated by those skilled in the art that, according to other embodiments of the invention, the vacuum chamber may have any other predetermined size and/or shape, e.g., as described below.

Figure 17:
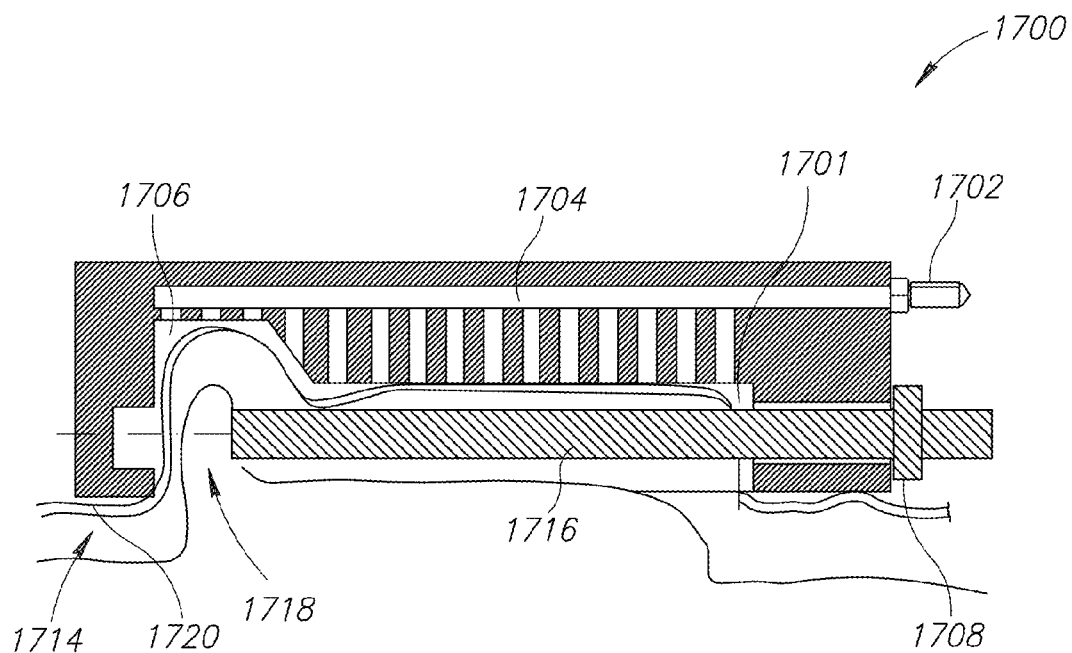
FIG. 17 is a schematic illustration of a dermal harvesting apparatus according to another exemplary embodiment of the invention.

Reference is now made to FIG. 17, which schematically illustrates a dermal harvesting apparatus 1700 according to another exemplary embodiment of the invention.

Apparatus 1700 may include a vacuum chamber 1701 including an elevated protrusion 1706. Elevated protrusion 1706 may have a predetermined size and/or shape adapted, for example, to enable the creation of a "plateau" of a single layer of skin tissue in a generally flat orientation, elevated above the trajectory of a coring tube 1716. For example, section 1706 may be higher than other sections of chamber 1701, such that a fat layer 1718 may be drawn into section 1706 and supported along the trajectory of coring tube 1716. As a result, after harvesting a DMO of a predetermined length, coring tube 1716 may be slightly advanced into fat layer 1718, thus separating the harvested DMO from tissue surrounding the DMO. The harvested DMO may remain within coring tube 1716 as it is withdrawn from the body. The configuration of Apparatus 1700 may eliminate the need for forming an "exit" incision in the skin, e.g., as described above, thus enabling the harvesting of a DMO with only a single incision.

According to some exemplary embodiments of the invention, apparatus 1700 may also include a drill stopper 1708 to enable manually advancing coring tube 1716 for a predetermined distance along chamber 1701, e.g., to a position in which coring tube 1716 has slightly advanced into fat tissue 1718.

Figure 18:
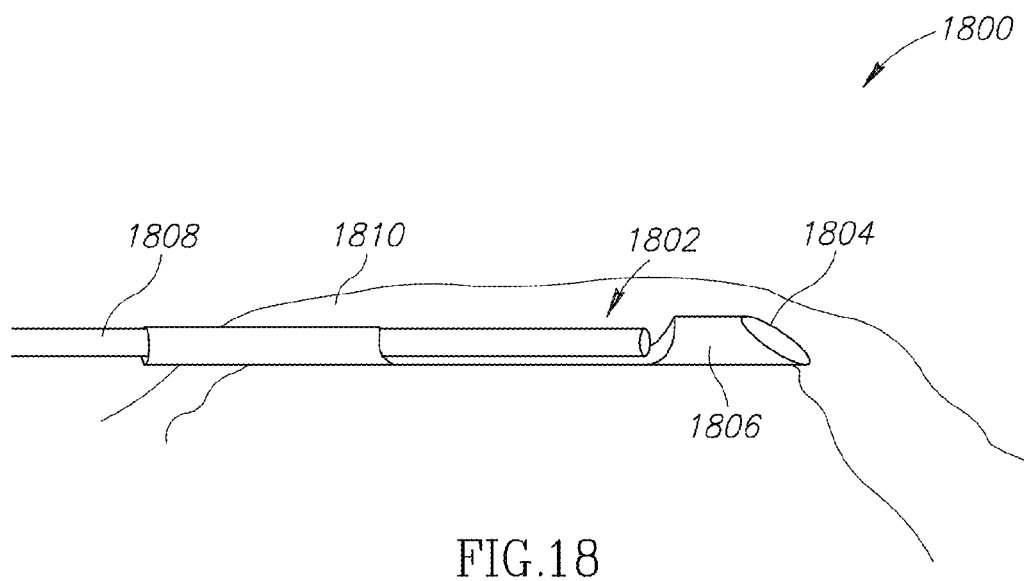
FIG. 18 is a schematic illustration of a harvesting apparatus according to yet another exemplary embodiment of the invention.
Figure 19:
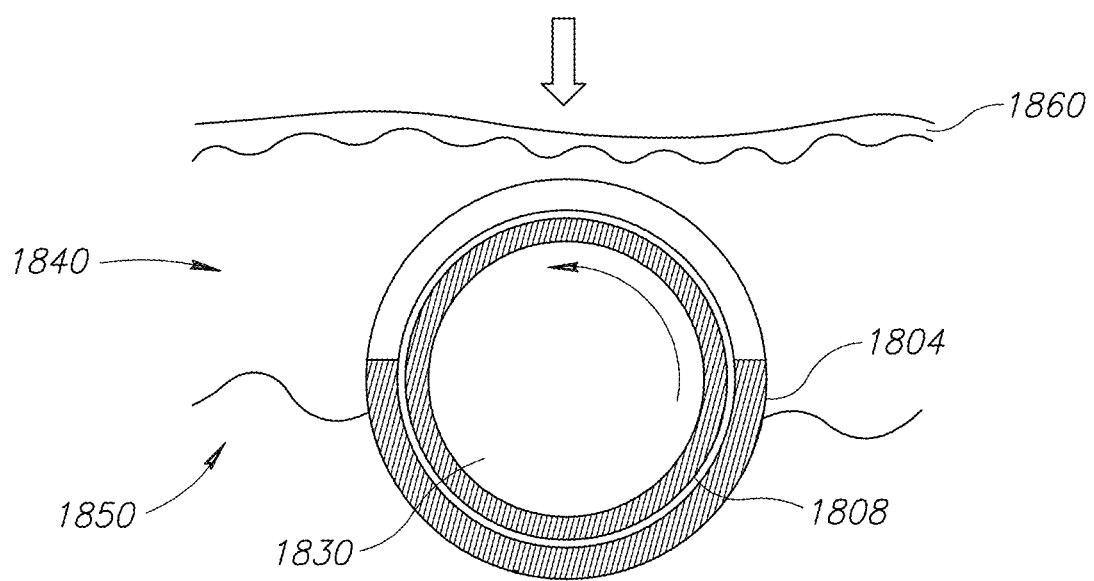
FIG. 19 is a schematic illustration of implementing the harvesting apparatus of FIG. 18 for harvesting a DMO.

Reference is now made to FIG. 18, which schematically illustrates a harvesting apparatus 1800, according to yet another exemplary embodiment of the invention, and to FIG. 19, which schematically illustrates a cross sectional view of apparatus 1800 being implemented for harvesting a DMO 1830.

According to some exemplary embodiments, core biopsy devices with similarities to the devices used, for example, in breast cancer biopsy applications, as described below, may be utilized for harvesting a DMO. Apparatus 1800 may include a cutting tool 1808, e.g., as described above, and a Subcutaneous Harvest Trocar (HST) 1806, e.g., a hypodermic needle with a sharpened tip 1804 and a suitable inner diameter, e.g., being slightly larger than the outer diameter of cutting tool 1808, such that cutting tool 1808 may be inserted into and substantially coaxially within HST 1806. HST 1806 may include a notch cutout ("window") 1802 of a suitable depth, e.g., 1 mm or more, and a suitable length, e.g., substantially equal to the desired length of the DMO to be harvested.

According to the exemplary embodiments of FIG. 18, a single incision, e.g., lance cut, may be formed, e.g., using a scalpel blade, through which HST 1806 may be inserted together with cutting tool 1808, e.g., as a single unit, at the desired position underneath or in the skin, preferably in the subcutaneous space with notch 1802 oriented upwards towards dermis layer 1840. Cutting tool 1801 may be positioned within HST 1806 during penetration such that window cutout 1802 may be "closed" to allow a generally smooth penetration of HST 1806. Tool 1808 and HST 1806 inserted therein may run along the subcutaneous interface for the length of notch 1802, and end 1804 may not exit through the skin surface. Once appropriately positioned, tool 1808 may be retracted to expose notch 1802 and allow for dermal tissue to substantially fill the notch. Appropriate pressure on the skin surface may be applied, e.g., using a suitable clamping tool, for example, as described above with reference to FIG. 12, and/or a vacuum condition may be applied from within HST 1802 by a vacuum manifold (not shown), e.g., located under notch cutout 1802, to assist the dermis to substantially fill notch 1802. Tool 1808 may be connected to a motor, e.g., as described above, to rotate tool 1808 at a rotational speed appropriate for cutting of the dermal tissue, for example, a relatively high rotational speed, for example, a speed higher than 1,000 RPM, e.g., between 1,000 RPM and 10,000 RPM. For example, tool 1808 may be rotated at a rotational speed higher than 2,000 RPM, e.g., approximately 7,000 RPM. Tool 1808 may then be advanced e.g., manually or automatically, for example, until it passes beyond the end of window cutout 1802, to cut DMO 1830 within notch 1802. When complete, the forward and rotational movements of tool 1808 may be stopped, and cutting tool 1808 may be retracted with harvested DMO 1830 within it. SHT 1806 may then be removed from the harvest site. DMO 1830 may be removed from cutting tool 1808, e.g., using a syringe to flush sterile fluid, for example saline, through tool 1808, or a vacuum source to draw out DMO 1830 from a back end (not shown) of cutting tool 1808.

It will be appreciated by those skilled in the art that apparatus 1800 may enable harvesting of the DMO by forming only one incision. Furthermore, apparatus 1800 may be efficiently applied for harvesting a DMO from areas having relatively thick skin, e.g., from a region of the donor's back.

It will be appreciated by those skilled in the art that the harvesting methods and/or apparatuses according to embodiments of the invention, e.g., as described above, may include introducing thin tissue cutting devices within the dermis. Thus, the harvesting methods and/or apparatuses according to embodiments of the invention may enable harvesting the DMO with relatively minimal damage to the outer skin surface, and therefore may provide a minimally invasive method of harvesting the desired tissues.

Although some embodiments of the invention described herein may refer to methods and/or apparatuses for harvesting a DMO, it will be appreciated by those skilled in the art that according to other embodiments of the invention at least some of the methods and/or apparatuses may be implemented for any other procedures, e.g., plastic surgical procedures, dermatological procedures, or any other procedures including harvesting of tissues. For example, the methods and/or apparatuses according to embodiments of the invention may be implemented for harvesting dermal tissue to be used, e.g., in a subsequent implantation, as filler material.

According to some embodiments of the present invention, a system and method are provided for ex-vivo ("in vitro") handling or processing of dermal micro-organs. Dermal tissue that has been harvested as a direct MO may be left on their inner guide as a mount for the MO. In these embodiments, the inner guide may be used to maintain position and orientation of the MOs during subsequent processing. In other embodiments, the dermal MOs may be removed from the inner guide and directly placed into tissue culture wells or transduction chambers of a bioreactor, as described in detail below, e.g., with reference to FIG. 22. In some embodiments, e.g., if the DMO remains in the coring tube as it is withdrawn from the skin, the DMO may be flushed out of the coring tube by the use of biologically compatible fluid, e.g., saline or growth medium, applied to the back end of the coring tube. The flushing of the DMO may be such that it is flushed directly into a chamber of the bioreactor, e.g., as described below. Alternatively, vacuum may be applied to a back end of the coring tube to "draw out" the DMO, e.g., directly into a chamber of the bioreactor.

According to some embodiments of the present invention, a system and method are provided for implantation of DTMOs. After producing and/or processing of a DMO, for example, by genetically modifying the DMO, the modified DMO or DTMO may be implanted back into the patient, for example, for protein or RNA based therapy. The number of full or partial DTMOs that are implanted may be determined by the desired therapeutic dosing of the secreted protein. DTMOs may be implanted subcutaneously or at any other locations within the body. Subcutaneous implantation by use of a needle trocar, for example, may enable the DTMO to remain in a linear form in the subcutaneous space. The linear form of implantation may help facilitate localization in case later ablation of the DTMO is required, for example, in order to stop treatment or reduce the dose of therapeutic protein. Other known geometrical implantation patterns could be used. The linear implantation may also assist in the integration of the dermal tissue to the surrounding tissue.

Figure 20:
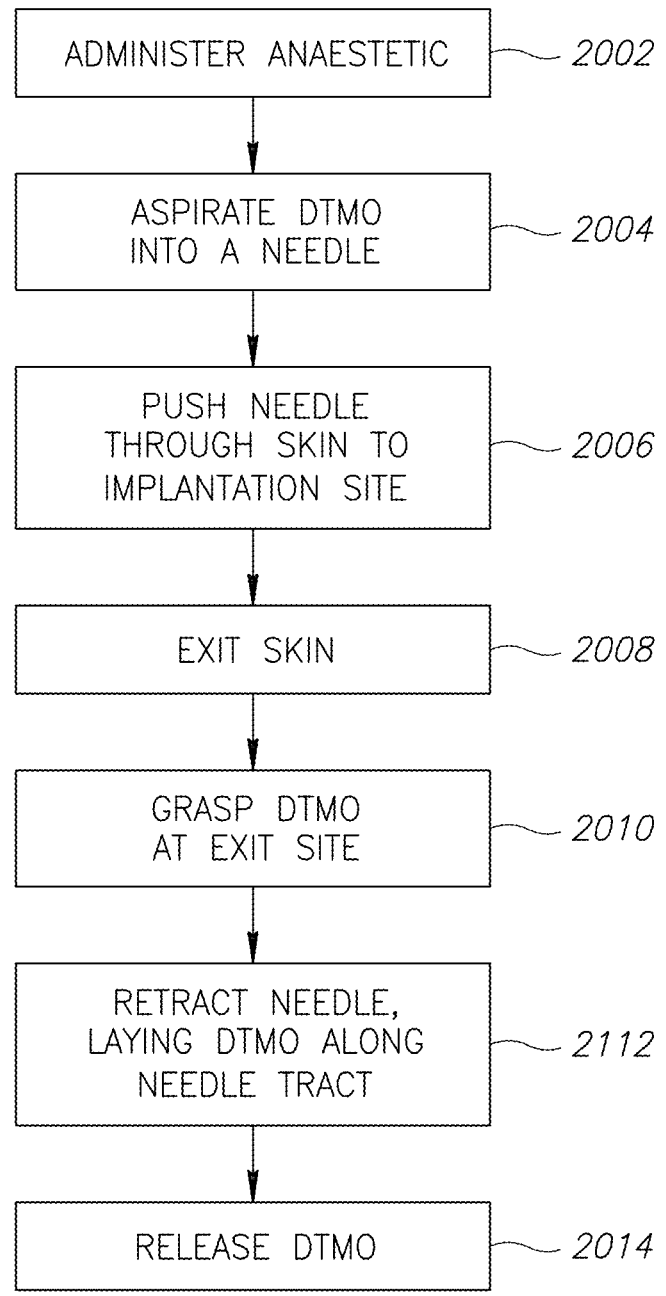
FIG. 20 is a flow chart illustrating a DTMO implanting method, according to some embodiments of the present invention.

Reference is now made to FIG. 20, which schematically illustrates a flowchart of a method of implanting a DTMO according to some exemplary embodiments of the invention.

As indicated at block 2002 a local anesthetic may be optionally administered at an intended implantation site.

As indicated at block 2004, according to some exemplary embodiments of the invention, the DTMO, optionally together with surrounding sterile saline fluid may be aspirated into a carrier, for example, an implantation needle, e.g., attached to a syringe. The needle may have any suitable diameter, for example, between 17-gauge and 12-gauge. Optionally, a tip of the needle may have a short extension of silicon tubing, or the like, affixed to it, to facilitate the aspiration of the DTMO into the needle cannula while retracting the plunger of the syringe.

As indicated at block 2006, with the loaded DTMO, the implantation needle, may be pushed into the skin, e.g., without the silicon tubing extension, into the subcutaneous destination, along a distance approximately equivalent to the length of the DTMO.

As indicated at block 2008, according to some embodiments, the implantation needle may exit through the skin surface at a distal end of the implantation site.

According to some exemplary embodiments of the invention, the method may include applying pressure on the aspirated dermal therapeutic micro-organ such that the dermal therapeutic micro-organ exits from the carrier into the implantation site.

As indicated at block 2010, the tip of the DTMO may be grasped at the exit point with a gripping tool, for example tweezers.

As indicated at block 2012, the implantation needle may be retracted through the subcutaneous space, releasing the DTMO from the implantation needle and laying the DTMO linearly along the needle tract. Assistance may be given to help release the DTMO, if needed, for example by gently pushing down on the syringe plunger during retraction.

As indicated at block 2014, once the DTMO has been left in place, the tip of the DTMO may be released by the gripping tool.

According to some embodiments of the present invention, a system and method are provided for in-vivo demarcation and localization of the implanted dermal micro-organs. Identification of the location of a subcutaneous implantation or implantation at any other location in the body, of processed tissue, such as a DTMO, may be important, for example, in the case where it is necessary to stop the protein treatment, or to decrease the dosage of the secreted protein. For example, termination or titration of dosage may be performed by removing one or more DTMOs entirely and/or by ablating one, a portion of one, or more than one of the implanted DTMOs. In order to identify a subcutaneously implanted DTMO, according to one embodiment, the DTMO may be colored prior to implantation by an inert, biocompatible ink or stain containing, for example, a chromophore, which may be visible to the naked eye or may require special illumination conditions to visualize it. In this way a DTMO may be distinguished from its surrounding tissue by visual inspection and/or by use of enhanced imaging means.

According to one embodiment, the peripheral surface of a DTMO may be coated with, for example, biocompatible carbon particles, biocompatible tattoo ink, or other suitable materials. Once implanted subcutaneously, the DTMO may be visible with the naked eye or with a suitable enhanced imaging device. Other ways to enhance the visibility of an implanted DTMO may include using a strong light source above the skin surface, or pinching the skin and directing the light source at the skin from one side, such that the skin may appear translucent and the dyed DTMO may be more visible.

Alternatively, the stain may be fluorescent, visible only when illuminated using UV light, such as using fluorescent plastic beads.

According to another embodiment, the location of a subcutaneously implanted DTMO may be identified by co-implanting a biocompatible structure along with the DTMO. An example of such a biocompatible structure is a non-absorbable single stranded nylon suture commonly used in many surgical procedures. Such a suture may be implanted in the same implantation tract with the DTMO, or may be implanted directly above the DTMO in the upper dermis, such that the spatial location of the DTMO may be determined by the suture location. Further, the depth of the DTMO may be known to be at the depth of the subcutaneous space. The suture may be visible to the naked eye, observed with the assistance of illumination means, and/or observed with the aid of other suitable imaging means, such as ultrasound. Alternatively, the suture can be fluorescent, and visible through the skin under appropriate UV illumination. The suture may alternatively be of an absorbable material, so that it may enable determination of localization for a desired period of time, such as a few months.

According to another embodiment, the DTMO may be genetically modified or engineered to include a gene to express a fluorescent marker or other marker capable of being visualized. For example, the DTMO can be modified with the GFP (Green Fluorescent Protein) gene or Luciferase reported gene, which, for example, may be expressed along with the gene for the therapeutic protein. In this manner, the DTMO may be visualized non-invasively using appropriate UV or other suitable illumination and imaging conditions.

According to some embodiments of the present invention, a system and method are provided for removal or ablation of implanted DTMOs. In a case, for example, where DTMO-based therapy to a patient must be terminated, or if the protein secretion must be decreased, each implanted DTMO may be partially or entirely removed, or partially or entirely ablated. One embodiment for removal of a DTMO is by means of a coring tube similar to, or slightly larger in diameter than, that used for direct harvesting of the DMO.

Figure 21:
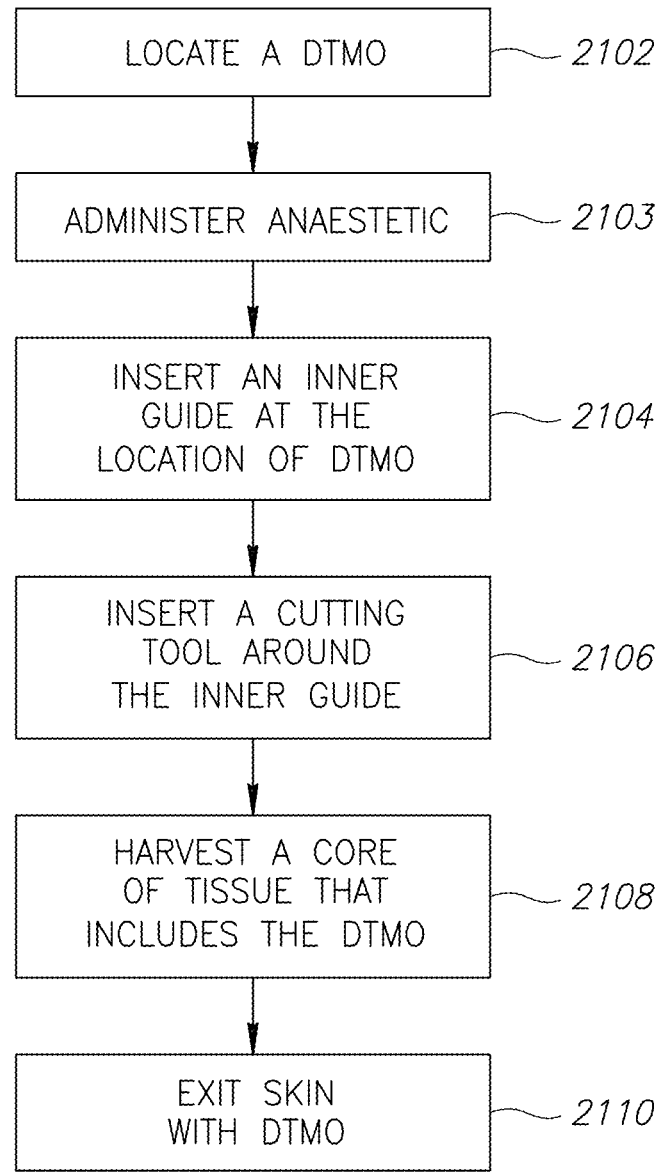
FIG. 21 is a flow chart illustrating a DTMO ablating method, according to some embodiments of the present invention.

As can be seen with reference to FIG. 21, at block 2102 the location of the implanted subcutaneous DTMO may be determined. At block 2103, a local anesthetic may be optionally administered at the site of DTMO removal. At block 2104 an inner guide may be inserted subcutaneously along the length of the DTMO, to harvest a core of tissue, which includes the DTMO. At block 2106 a coring needle, of the same or larger diameter than that of the implantation needle (for example, 11-gauge or similar), may be inserted concentrically over the inner guide. At block 2108 a core of tissue that includes the DTMO may be harvested. At block 2110 the inner guide with the cored of tissue and the coring needle may be extracted from the skin, with the DTMO. In one embodiment, such a coring approach may be combined with vacuum suction to help remove the cut material from the body.

According to an embodiment of the present invention, minimally invasive or non-invasive methods of ablating the DTMO in-situ may be used to make the procedure less traumatic and less invasive for the patient. In one embodiment, in the case of the dyed DTMO, a laser, for example, a non-invasive Yag laser may be used. The energy of the Yag laser, for example, may be selectively absorbed by the chromophore, such that the energy is primarily directed to the DTMO, with minimum damage caused to the surrounding tissue. Other light energy sources may also be used.

According to another embodiment, the DTMO may be ablated by delivering destructive energy from a minimally invasive probe inserted into the subcutaneous space along the length of the DTMO. Such a probe may enable delivery of a variety of energy types, including radio frequency, cryogenic, microwave, resistive heat, etc. A co-implanted structure, such as a suture, may be used to determine the location of the DTMO, thereby enabling the probe to be inserted subcutaneously, for example, along or directly below the suture. In such a case, for example, the destructive energy may be delivered while the suture is still in place. Alternatively, the suture may be removed after placement of the probe and before delivery of the destructive energy. The amount of energy applied may be either that required to denature the proteins in the tissue such as during coagulation by diathermy. Additionally or alternatively, the amount of energy applied may be as much as is used in electro-surgical cutting devices, which char tissue. Of course, other means of localization and other means of delivering destructive energy may be used.

After a DMO is harvested, e.g., according to embodiments of the present invention, the DMO is optionally genetically altered. Any methodology known in the art can be used for genetically altering the tissue. One exemplary method is to insert a gene into the cells of the tissue with a recombinant viral vector. Any one of a number of different vectors can be used, such as viral vectors, plasmid vectors, linear DNA, etc., as known in the art, to introduce an exogenous nucleic acid fragment encoding for a therapeutic agent into target cells and/or tissue. These vectors can be inserted, for example, using any of infection, transduction, transfection, calcium-phosphate mediated transfection, DEAE-dextran mediated transfection, electroporation, liposome-mediated transfection, biolistic gene delivery, liposomal gene delivery using fusogenic and anionic liposomes (which are an alternative to the use of cationic liposomes), direct injection, receptor-mediated uptake, magnetoporation, ultrasound and others as known in the art. This gene insertion is accomplished by introducing the vector into the vicinity of the DMO so that the vector can react with the cells of the DMO. Once the exogenous nucleic acid fragment has been incorporated into the cells, the production and/or the secretion rate of the therapeutic agent encoded by the nucleic acid fragment can be quantified.

According to some exemplary embodiments of the invention, the genetic modification of the DMO may modify the expression profile of an endogenous gene. This may be achieved, for example, by introducing an enhancer, or a repressible or inducible regulatory element for controlling the expression of the endogenous gene.

In another embodiment, the invention provides a method of delivering a gene product of interest into a subject by implanting the genetically modified DMO of the invention into a subject.

As indicated above, the DMO may be in contact with a nutrient solution during the process. Thus, a therapeutic agent generated by the DTMO may be secreted into the solution where its concentration can be measured. The gene of interest may be any gene which encodes to any RNA molecule (sense or antisense), peptide, polypeptide, glycoprotein, lipoprotein or combination thereof or to any other post modified polypeptide. In one embodiment of the invention, the gene of interest may be naturally expressed in the tissue sample. In another embodiment of this invention, the tissue sample may be genetically engineered so that at least one cell will express the gene of interest, which is either not naturally expressed by the cell or has an altered expression profile within the cell.

As used herein, the term "nucleic acid" refers to polynucleotide or to oligonucleotides such as deoxyribonucleic acid (DNA), and, where appropriate, ribonucleic acid (RNA) or mimetic thereof. The term should also be understood to include, as equivalents, analogs of either RNA or DNA made from nucleotide analogs, and, as applicable to the embodiment being described, single (sense or antisense) and double-stranded polynucleotide. This term includes oligonucleotides composed of naturally occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

As is known to those of skill in the art, the term "protein", "peptide" or "polypeptide" means a linear polymer of amino acids joined in a specific sequence by peptide bonds. As used herein, the term "amino acid" refers to either the D or L stereoisomer form of the amino acid, unless otherwise specifically designated. Also encompassed within the scope of this invention are equivalent proteins or equivalent peptides, e.g., having the biological activity of purified wild type tumor suppressor protein. "Equivalent proteins" and "equivalent polypeptides" refer to compounds that depart from the linear sequence of the naturally occurring proteins or polypeptides, but which have amino acid substitutions that do not change it's biologically activity. These equivalents can differ from the native sequences by the replacement of one or more amino acids with related amino acids, for example, similarly charged amino acids, or the substitution or modification of side chains or functional groups.

The protein, peptide, polypeptide glycoprotein or lipoprotein can be, without being limited, any of the following proteins or various combinations thereof: protease, a lipase, a ribonuclease, a deoxyribonuclease, a blood clotting factor, a cytochrome p450 enzyme, a transcription factor, a MHC component, a cytokine, an interleukin, a BMP, a chemokine, a growth factor, a hormone, an enzyme, a monoclonal antibody, a single chain antibody, an oxidoreductas, a p450, a peroxydase, a hydrogenase, a dehydrogenas, a catalase, a transferase, a hydrolase, an isomerase, a ligase, an aminoacyl-trna synthetase, a kinase, a phosphoprotein, a mutator transposon, an oxidoreductas, a cholinesterase, a glucoamylase, a glycosyl hydrolase, a transcarbamylase, a nuclease, a meganuclease, a ribonuclease, an atpase, a peptidase, a cyclic nucleotide synthetase, a phosphodiesterase, a phosphoprotein, a DNA or RNA associated protein, a high mobility group protein, a paired box protein, a histone, a polymerase, a DNA repair protein, a ribosomal protein, an electron transport protein, a globin, a metallothionein, a membrane transport protein, a structural protein, a receptor, a cell surface receptor, a nuclear receptor, a G-protein, an olfactory receptor, an ion channel receptor, a channel, a tyrosine kinase receptor, a cell adhesion molecule or receptor, a photoreceptor, an active peptide, a protease inhibitor, a chaperone, a chaperonin, a stress associated protein, a transcription factor and a chimeric protein.

In one embodiment the amount of protein secreted by the DMO of the invention is at least 1.6 µg/DTMO/day at the pre-implantation day.

In one embodiment of this invention, the gene of interest may encode to erythropoietin or to equivalent protein thereof.

In another embodiment of the invention, the gene of interest may encode, without limitation, to any of the following proteins, any combination of the following proteins and any equivalents thereof: insulin, trypsinogen, chymotrypsinogen, elastase, amylase, serum thymic factor, thymic humoral factor, thymopoietin, gastrin, secretin, somatostatin, substance P, growth hormone, a somatomedin, a colony stimulating factor, erythropoietin, epidermal growth factor, hepatic erythropoietic factor (hepatopoietin), a liver-cell growth factor, an interleukin, a negative growth factor, fibroblast growth factor and transforming growth factor of the β family, Interferon α, Interferon β Interferon γ, human growth hormone, G-CSF, GM-CSF, TNF-receptor, PDGF, AAT, VEGF, Super oxide dismutase, Interleukin, TGF-β, NGF, CTNF, PEDF, NMDA, AAT, Actin, Activin beta-A, Activin beta-B, Activin beta-C Activin beta-E Adenosine Deaminase adenosine deaminase Agarase-Beta, Albumin HAS Albumin, Alcohol Dehydrogenase Aldolase, Alfimeprase Alpha 1-Antitrypsin Alpha Galactosidase Alpha-1-acid Glycoprotein (AGP), Alpha-1-Antichymotrypsin, Alpha-1-Antitrypsin AT, Alpha-1-microglobulin A1M, Alpha-2-Macroglobulin A2M, Alpha-Fetoprotein, Alpha-Galactosidase, Amino Acid Oxidase, D-, Amino Acid Oxidase, L-, Amylase, Alpha, Amylase, Beta, Angiostatin, Angiotensin, Converting Enzyme, Ankyrin, Apolipoprotein, APO-SAA, Arginase, Asparaginase, Aspartyl Aminotransferase, Atrial Natriuretic factor (Anf), Atrial Natriuretic Peptide, Atrial natriuretic peptide (Anp), Avidin, Beta-2-Glycoprotein 1, Beta-2-microglobulin, Beta-N-Acetylglucosaminidase B-NAG, beta amyloid, Brain natriuretic protein (Bnp), Brain-derived neurotrophic factor (BDNF), Cadherin E, Calc a, Calc b, Calcitonin, Calcyclin, Caldesmon, Calgizzarin, Calgranulin A, Calgranulin C, Calmodulin, Calreticulin, Calvasculin, Carbonic Anhydrase, Carboxypeptidase, Carboxypeptidase A, Carboxypeptidase B, Carboxypeptidase Y, CARDIAC TROPONIN I, CARDIAC TROPONIN T, Casein, Alpha, Catalase, Catenins, Cathepsin D, CD95L, CEA, Cellulase, Centromere Protein B, Ceruloplasmin, Ceruplasmin, cholecystokinin, Cholesterol Esterase, Cholinesterase, Acetyl, Cholinesterase Butyryl, Chorionic Gonadotrophin (HCG), Chorionic Gonadotrophin Beta CORE (BchCG), Chymotrypsin, Chymotrypsinogen, Chymotrypsin, Chymotrypsin, Creatin kinase, K-BB, CK-MB (Creatine Kinase-MB), CK-MM, Clara cell phospholipid binding protein, Clostripain, Clusterin, CNTF, Collagen, Collagenase, Collagens (type 1-VI), colony stimulating factor, Complement C1q Complement C3, Complement C3a, Complement C3b-alpha, Complement C3b-beta, Complement C4, Complement C5, Complement Factor B, Concanavalin A, Corticoliberin, Corticotrophin releasing hormone, C-Reactive Protein (CRP), C-type natriuretic peptide (Cnp), Cystatin C, D-Dimer, Delta 1, Delta-like kinase 1 (Dlk1), Deoxyribonuclease, Deoxyribonuclease I, Deoxyribonuclease II, Deoxyribonucleic Acids, Dersalazine, Dextranase, Diaphorase, DNA Ligase, T4, DNA Polymerase I, DNA Polymerase, T4, EGF, Elastase, Elastase, Elastin, Endocrine-gland-derived vascular endothelial growth factor (EG-VEGF), Elastin Endothelin Elastin Endothelin 1 Elastin Eotaxin Elastin, Epidermal growth factor (EGF), Epithelial Neutrophil Activating Peptide-78 (ENA-78), Erythropoietin (Epo), Estriol, Exodus, Factor IX, Factor VIII, Fatty acid-binding protein, Ferritin, fibroblast growth factor, Fibroblast growth factor 10, Fibroblast growth factor 11, Fibroblast growth factor 12, Fibroblast growth factor 13, Fibroblast growth factor 14, Fibroblast growth factor 15, Fibroblast growth factor 16, Fibroblast growth factor 17, Fibroblast growth factor 18, Fibroblast growth factor 19, Fibroblast growth factor 2, Fibroblast growth factor 20, Fibroblast growth factor 3, Fibroblast growth factor 4, Fibroblast growth factor 5, Fibroblast growth factor 6, Fibroblast growth factor 7, Fibroblast growth factor 8, Fibroblast growth factor 9, Fibronectin, focal-adhesion kinase (FAK), Follitropin alfa, Galactose Oxidase, Galactosidase, Beta, gamaIP-10, gastrin, GCP, G-CSF, Glial derived Neurotrophic Factor (GDNF), Glial fibrillary acidic Protein, Glial filament protein (GFP), glial-derived neurotrophic factor family receptor (GFR), globulin, Glucose Oxidase, Glucose-6-Phosphate Dehydrogenase, Glucosidase, Alpha, Glucosidase, Beta, Glucuronidase, Beta, Glutamate Decarboxylase, Glyceraldehyde-3-Phosphate Dehydrogenase, Glycerol Dehydrogenase, Glycerol Kinase, Glycogen Phosphorylase ISO BB, Granulocyte Macrophage Colony Stimulating Factor (GM-CSF), growth stimulatory protein (GRO), growth hormone, Growth hormone releasing hormone, Hemopexin, hepatic erythropoietic factor (hepatopoietin), Heregulin alpha, Heregulin beta 1, Heregulin beta 2, Heregulin beta 3, Hexokinase, Histone, Human bone morphogenetic protein, Human relaxin H2, Hyaluronidase, Hydroxysteroid Dehydrogenase, Hypoxia-Inducible Factor-1 alpha (HIF-1 Alpha), I-309/TCA-3, IFN alpha, IFN beta, IFN gama, IgA, IgE, IgG, IgM, Insulin, Insulin Like Growth Factor I (IGF-I), Insulin Like Growth Factor II (IGF-II), Interferon, Interferon-inducible T cell alpha chemoattractant (I-TAC), Interleukin, Interleukin 12 beta, Interleukin 18 binding protein, Intestinal trefoil factor, IP10, Jagged 1, Jagged 2, Kappa light chain, Keratinocyte Growth Factor (KGF), Kiss1, La/SS-B, Lactate Dehydrogenase, Lactate Dehydrogenase, L-, Lactoferrin, Lactoperoxidase, lambda light chain, Laminin alpha 1, Laminin alpha 2, Laminin beta 1 Laminin beta 2, Laminin beta 3, Laminin gamma 1, Laminin gamma 2, LD78beta, Leptin, leucine Aminopeptidase, Leutenizing Hormone (LH), LIF, Lipase, liver-cell growth factor, liver-expressed chemokine (LEC), LKM Antigen, TNF, TNF beta, Luciferase, Lutenizing hormone releasing hormone, Lymphocyte activation gene-1 protein (LAG-1), Lymphotactin, Lysozyme, Macrophage Inflammatory Protein 1 alpha (MIP-1 Alpha), Macrophage-Derived Chemokine (MDC), Malate Dehydrogenase, Maltase, MCP (macrophage/monocyte chemotactic protein)-1, 2 and 3, 4, M-CSF, MEC (CCL28), Membrane-type frizzled-related protein (Mfrp), Midkine, MIF, MIG (monokine induced by interferon gamma), MIP 2 to 5, MIP-1beta, Mp40; P40 T-cell and mast cell growth factor, Myelin Basic Protein Myeloperoxidase, Myoglobin, Myostatin Growth Differentiation Factor-8 (GDF-8), Mysoin, Mysoin LC, Mysoin HC, ATPase, NADase, NAP-2, negative growth factor, nerve growth factor (NGF), Neuraminidase, Neuregulin 1, Neuregulin 2, Neuregulin 3, Neuron Specific Enolase, Neuron-Specific Enolase, neurotrophin-3 (NT-3), neurotrophin-4 (NT-4), Neuturin, NGF, NGF-Beta, Nicastrin, Nitrate Reductase, Nitric Oxide Synthesases, Nortestosterone, Notch 1, Notch 2, Notch 3, Notch 4, NP-1, NT-1 to 4, NT-3 Tpo, NT-4, Nuclease, Oncostatin M, Ornithine transcarbamoylase, Osteoprotegerin, Ovalbumin, Oxalate Decarboxylase, P16, Papain, PBP, PBSF, PDGF, PDGF-AA, PDGF-AB, PDGF-BB, PEDF, Pepsin, Peptide YY (PYY), Peroxidase, Persephin, PF-4, P-Glycoprotein, Phosphatase, Acid, Phosphatase, Alkaline, Phosphodiesterase I, Phosphodiesterase II, Phosphoenolpyruvate Carboxylase, Phosphoglucomutase, Phospholipase, Phospholipase A2, Phospholipase A2, Phospholipase C, Phosphotyrosine Kinase, Pituitary adenylate cyclase activating polypeptide, Placental Lactogen, Plakoglobin, Plakophilin, Plasma Amine Oxidase, Plasma retinol binding protein, Plasminogen, Pleiotrophin (PTN), PLGF-1, PLGF-2, Pokeweed Antiviral Toxin, Prealbumin, Pregnancy assoc Plasma Protein A, Pregnancy specific beta I glycoprotein (SPI), Prodynorphin, Proenkephalin, Progesterone Proinsulin, Prolactin, Pro-melanin-concentrating hormone (Pmch), Pro-opiomelanocortin, proorphanin, Prostate Specific Antigen PSA, Prostatic Acid Phosphatase PAP, Prothrombin, PSA-A1, Pulmonary surfactant protein A, Pyruvate Kinase, Ranpirnase, RANTES, Reelin, Renin, Resistin, Retinol Binding Globulin RBP, RO SS-A 60 kda, RO/SS-A 52 kda, S100 (human brain) (BB/AB), S100 (human) BB homodimer, Saposin, SCF, SCGF-alpha, SCGF-Beta, SDF-1 alpha, SDF-I Beta, Secreted frizzled related protein 1 (Sfrp 1), Secreted frizzled related protein 2 (Sfrp2), Secreted frizzled related protein 3 (Sfrp3), Secreted frizzled related protein 4 (Sfrp4), Secreted frizzled related protein 5 (Sfrp5), secretin, serum thymic factor, Binding Globulin (SHBG), somatomedin, somatostatin, Somatotropin, s-RankL, substance P, Superoxide Dismutase, TGF alpha, TGF beta, Thioredoxin, Thrombopoietin (TPO), Thrombospondin 1, Thrombospondin 2, Thrombospondin 3, Thrombospondin 4, Thrombospondin 5, Thrombospondin 6, Thrombospondin 7, thymic humoral factor, thymopoietin, thymosin a1, Thymosin alpha-1, Thymus and activation regulated chemokine (TARC), Thymus-expressed chemokine (TECK), Thyroglobulin Tg, Thyroid Microsomal Antigen, Thyroid Peroxidase, Thyroid Peroxidase TPO, Thyroxine (T4), Thyroxine Binding Globulin TBG, TNFalpha, TNF receptor, Transferin, Transferrin receptor, transforming growth factor of the b family, Transthyretin, Triacylglycerol lipase, Triiodothyronine (T3), Tropomyosin alpha, tropomyosin-related kinase (trk), Troponin C, Troponin I, Troponin T, Trypsin, Trypsin Inhibitors, Trypsinogen, TSH, Tweak, Tyrosine Decarboxylase, Ubiquitin, UDP glucuronyl transferase, Urease, Uricase, Urine Protein 1, Urocortin 1, Urocortin 2, Urocortin 3, Urotensin II, Vang-like 1 (Vangl1), Vang-like 2 (Vangl2), Vascular Endothelial Growth Factor (VEGF), Vasoactive intestinal peptide precursor, Vimentin, Vitamine D binding protein, Von Willebrand factor, Wnt1, Wnt10a, Wnt10b, Wnt11, Wnt12, Wnt13, Wnt14, Wnt15, Wnt16, Wnt2, Wnt3, Wnt3a, Wnt4, Wnt5a, Wnt5b, Wnt6, Wnt7a, Wnt7b, Wnt8a, Wnt8b, Wnt9, Xanthine Oxidase, Clara cell phospholipid binding protein, Clostripain, Clusterin, CNTF, Collagen, Collagenase, Collagens (type 1-VI), colony stimulating factor, Complement C1q Complement C3, Complement C3a, Complement C3b-alpha, Complement C3b-beta, Complement C4, Complement C5, Complement Factor B, Concanavalin A, Corticoliberin, Corticotrophin releasing hormone, C-Reactive Protein (CRP), C-type natriuretic peptide (Cnp), Cystatin C, D-Dimer, Delta 1, Delta-like kinase 1 (Dlk1), Deoxyribonuclease, Deoxyribonuclease I, Deoxyribonuclease II, Deoxyribonucleic Acids, Dersalazine, Dextranase, Diaphorase, DNA Ligase, T4, DNA Polymerase I, DNA Polymerase, T4, EGF, Elastase, Elastase, Elastin, Endocrine-gland-derived vascular endothelial growth factor (EG-VEGF), Elastin Endothelin Elastin Endothelin 1 Elastin Eotaxin Elastin, Epidermal growth factor (EGF), Epithelial Neutrophil Activating Peptide-78 (ENA-78), Erythropoietin (Epo), Estriol, Exodus, Factor IX, Factor VIII, Fatty acid-binding proteinFerritin Ferritin, fibroblast growth factor, Fibroblast growth factor 10, Fibroblast growth factor 11, Fibroblast growth factor 12, Fibroblast growth factor 13, Fibroblast growth factor 14, Fibroblast growth factor 15, Fibroblast growth factor 16, Fibroblast growth factor 17, Fibroblast growth factor 18, Fibroblast growth factor 19, Fibroblast growth factor 2, Fibroblast growth factor 20, Fibroblast growth factor 3, Fibroblast growth factor 4, Fibroblast growth factor 5, Fibroblast growth factor 6, Fibroblast growth factor 7, Fibroblast growth factor 8, Fibroblast growth factor 9, Fibronectin, focal-adhesion kinase (FAK), Follitropin alfa, Galactose Oxidase, Galactosidase, Beta, gamaIP-10, gastrin, GCP, G-CSF, Glial derived Neurotrophic Factor (GDNF), Glial fibrillary acidic Protein, Glial filament protein (GFP), glial-derived neurotrophic factor family receptor (GFR), globulin, Glucose Oxidase, Glucose-6-Phosphate Dehydrogenase, Glucosidase, Alpha, Glucosidase, Beta, Glucuronidase, Beta, Glutamate Decarboxylase, Glyceraldehyde-3-Phosphate Dehydrogenase, Glycerol Dehydrogenase, Glycerol Kinase, Glycogen Phosphorylase ISO BB, Granulocyte Macrophage Colony Stimulating Factor (GM-CSF), growth stimulatory protein (GRO), growth hormone, Growth hormone releasing hormone, Hemopexin, hepatic erythropoietic factor (hepatopoietin), Heregulin alpha, Heregulin beta 1, Heregulin beta 2, Heregulin beta 3, Hexokinase, Histone, Human bone morphogenetic protein, Human relaxin H2, Hyaluronidase, Hydroxysteroid Dehydrogenase, Hypoxia-Inducible Factor-1 alpha (HIF-1 Alpha), I-309/TCA-3, IFN alpha, IFN beta, IFN gama, IgA, IgE, IgG, IgM, Insulin, Insulin Like Growth Factor I (IGF-I), Insulin Like Growth Factor II (IGF-II), Interferon, Interferon-inducible T cell alpha chemoattractant (I-TAC), Interleukin, Interleukin 12 beta, Interleukin 18 binding protein, Intestinal trefoil factor, IP10, Jagged 1, Jagged 2, Kappa light chain, Keratinocyte Growth Factor (KGF), Kiss1, La/SS-B, Lactate Dehydrogenase, Lactate Dehydrogenase, L-, Lactoferrin, Lactoperoxidase, lambda light chain, Laminin alpha 1, Laminin alpha 2, Laminin beta 1 Laminin beta 2, Laminin beta 3, Laminin gamma 1, Laminin gamma 2, LD78beta, Leptin, leucine Aminopeptidase, Leutenizing Hormone (LH), LIF, Lipase, liver-cell growth factor, liver-expressed chemokine (LEC), LKM Antigen, TNFbeta, Luciferase, Lutenizing hormone releasing hormone, Lymphocyte activation gene-1 protein (LAG-1), Lymphotactin, Lysozyme, Macrophage Inflammatory Protein 1 alpha (MIP-1 Alpha), Macrophage-Derived Chemokine (MDC), Malate Dehydrogenase, Maltase, MCP (macrophage/monocyte chemotactic protein)-1, 2 and 3, 4, M-CSF, MEC (CCL28), Membrane-type frizzled-related protein (Mfrp), Midkine, MIF, MIG (monokine induced by interferon gamma), MIP 2 to 5, MIP-theta, Mp40; P40 T-cell and mast cell growth factor, Myelin Basic Protein Myeloperoxidase, Myoglobin, Myostatin Growth Differentiation Factor-8 (GDF-8), Mysoin, Mysoin LC, Mysoin HC, ATPase, NADase, NAP-2, negative growth factor, nerve growth factor (NGF), Neuraminidase, Neuregulin 1, Neuregulin 2, Neuregulin 3, Neuron Specific Enolase, Neuron-Specific Enolase, neurotrophin-3 (NT-3), neurotrophin-4 (NT-4), Neuturin, NGF, NGF-Beta, Nicastrin, Nitrate Reductase, Nitric Oxide Synthesases, Nortestosterone, Notch 1, Notch 2, Notch 3, Notch 4, NP-1, NT-1 to 4, NT-3 Tpo, NT-4, Nuclease, Oncostatin M, Omithine transcarbamoylase, Osteoprotegerin, Ovalbumin, Oxalate Decarboxylase, P16, Papain, PBP, PBSF, PDGF, PDGF-AA, PDGF-AB, PDGF-BB, PEDF, Pepsin, Peptide YY (PYY), Peroxidase, Persephin, PF-4, P-Glycoprotein, Phosphatase, Acid, Phosphatase, Alkaline, Phosphodiesterase I, Phosphodiesterase II, Phosphoenolpyruvate Carboxylase, Phosphoglucomutase, Phospholipase, Phospholipase A2, Phospholipase A2, Phospholipase C, Phosphotyrosine Kinase, Pituitary adenylate cyclase activating polypeptide, Placental Lactogen, Plakoglobin, Plakophilin, Plasma Amine Oxidase, Plasma retinol binding protein, Plasminogen, Pleiotrophin (PTN), PLGF-1, PLGF-2, Pokeweed Antiviral Toxin, Prealbumin, Pregnancy assoc Plasma Protein A, Pregnancy specific beta 1 glycoprotein (SPI), Prodynorphin, Proenkephalin, Progesterone Proinsulin, Prolactin, Pro-melanin-concentrating hormone (Pmch), Pro-opiomelanocortin, proorphanin, Prostate Specific Antigen PSA, Prostatic Acid Phosphatase PAP, Prothrombin, PSA-A1, Pulmonary surfactant protein A, Pyruvate Kinase, Ranpimase, RANTES, Reelin, Renin, Resistin, Retinol Binding Globulin RBP, RO SS-A 60 kda, RO/SS-A 52 kda, S100 (human brain) (BB/AB), S100 (human) BB homodimer, Saposin, SCF, SCGF-alpha, SCGF-Beta, SDF-1 alpha, SDF-1 Beta, Secreted frizzled related protein 1 (Sfrp1), Secreted frizzled related protein 2 (Sfrp2), Secreted frizzled related protein 3 (Sfrp3), Secreted frizzled related protein 4 (Sfrp4), Secreted frizzled related protein 5 (Sfrp5), secretin, serum thymic factor, Binding Globulin (SHBG), somatomedin, somatostatin, Somatotropin, s-RankL, substance P, Superoxide Dismutase, TGF alpha, TGF beta, Thioredoxin, Thrombopoietin (TPO), Thrombospondin 1, Thrombospondin 2, Thrombospondin 3, Thrombospondin 4, Thrombospondin 5, Thrombospondin 6, Thrombospondin 7, thymic humoral factor, thymopoietin, thymosin a1, Thymosin alpha-1, Thymus and activation regulated chemokine (TARC), Thymus-expressed chemokine (TECK), Thyroglobulin Tg, Thyroid Microsomal Antigen, Thyroid Peroxidase, Thyroid Peroxidase TPO, Thyroxine (T4), Thyroxine Binding Globulin TBG, TNFalpha, TNF receptor, Transferin, Transferrin receptor, transforming growth factor of the b family, Transthyretin, Triacylglycerol lipase, Triiodothyronine (T3), Tropomyosin alpha, tropomyosin-related kinase (trk), Troponin C, Troponin I, Troponin T, Trypsin, Trypsin Inhibitors, Trypsinogen, TSH, Tweak, Tyrosine Decarboxylase, Ubiquitin, UDP glucuronyl transferase, Urease, Uricase, Urine Protein 1, Urocortin 1, Urocortin 2, Urocortin 3, Urotensin II, Vang-like 1 (Vangl1), Vang-like 2 (Vangl2), Vascular Endothelial Growth Factor (VEGF), Vasoactive intestinal peptide precursor, Vimentin, Vitamine D binding protein, Von Willebrand factor, Wnt1, Wnt10a, Wnt10b, Wnt11, Wnt12, Wnt13, Wnt14, Wnt15, Wnt16, Wnt2, Wnt3, Wnt3a, Wnt4, Wnt5a, Wnt5b, Wnt6, Wnt7a, Wnt7b, Wnt8a, Wnt8b, Wnt9 and Xanthine Oxidase.

Following the genetic modification process, the tissue sample may be then analyzed in order to verify the expression of the gene of interest by the tissue sample. This could be done by any method known in the art, for example by ELISA detection of proteins or Northern blot for RNA. The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be expressed by a cell is not readily assayable, an expression system can first be optimized using a reporter gene linked to the regulatory elements and vector to be used. The reporter gene encodes a gene product which is easily detectable and, thus, can be used to evaluate efficacy of the system. Standard reporter genes used in the art include genes encoding β-galactosidase, chloramphenicol acetylm transferase, luciferase, GFP/EGFP and human growth hormone.

The invention contemplates, in one aspect, the use of the genetically modified DTMO for transplantation in an organism. As used herein the terms "administering", "introducing", "implanting" and "transplanting" may be used interchangeably and refer to the placement of the DTMO of the invention into a subject, e.g., an autologous, allogeneic or xenogeneic subject, by a method or route which results in localization of the DTMO at a desired site. The DTMO is implanted at a desired location in the subject in such a way that at least a portion of the cells of the DTMO remain viable. In one embodiment of this invention, at least about 5%, in another embodiment of this invention, at least about 10%, in another embodiment of this invention, at least about 20%, in another embodiment of this invention, at least about 30%, in another embodiment of this invention, at least about 40%, and in another embodiment of this invention, at least about 50% or more of the cells remain viable after administration to a subject. The period of viability of the cells after administration to a subject can be as short as a few hours, e.g., twenty-four hours, to a few days, to as long as a few weeks to months or years. To facilitate transplantation of the cell populations within a tissue which may be subject to immunological attack by the host, e.g., where xenogenic grafting is used, such as swine-human transplantations, the DTMO may be inserted into or encapsulated by biocompatible immuno-protected material such as rechargeable, non-biodegradable or biodegradable devices and then transplanted into the recipient subject. Gene products produced by such cells/tissue can then be delivered via, for example, polymeric devices designed for controlled delivery of compounds, e.g., drugs, including proteinaceous biopharmaceuticals. A variety of biocompatible polymers (including hydrogels, for example), including both biodegradable and non-degradable polymers, can be used to form an implant for the sustained release of a gene product of the cell populations of the invention at a particular target site. The generation of such implants is generally known in the art. See, for example, Concise Encyclopedia of Medical & Dental Materials, ed. By David Williams (MIT Press: Cambridge, Mass., 1990); the Sabel et al. U.S. Pat. No. 4,883,666; Aebischer et al. U.S. Pat. No. 4,892,538; Aebischer et al. U.S. Pat. No. 5,106,627; Lim U.S. Pat. No. 4,391,909; and Sefton U.S. Pat. No. 4,353,888. Cell populations within the DTMO of the present invention can be administered in a pharmaceutically acceptable carrier or diluent, such as sterile saline and aqueous buffer solutions. The use of such carriers and diluents is well known in the art.

The secreted protein such as, for example, without limitation, may be any protein according to the embodiments of the invention described above. The protein of interest may be, in one embodiment of this invention, erythropoietin. In another embodiment of this invention, the method of the invention may be used for the expression and secretion of each and any protein known in the art and combinations thereof. In addition, the method of the invention may be used for the expression of RNA molecules (sense or antisense)

Alternatively, the DMO, which includes genetically modified cells can be kept in vitro and the therapeutic agent, left in the supernatant medium surrounding the tissue sample, can be isolated and injected or applied to the same or a different subject.

Alternatively or additionally, a dermal micro-organ which includes a genetically modified cell can be cryogenically preserved by methods known in the art, for example, without limitation, gradual freezing (0.degree. C., −20.degree. C., −80.degree. C., −196.degree. C.) in DMEM containing 10% DMSO, immediately after being formed from the tissue sample or after genetic alteration.

In accordance with an aspect of some embodiments of the invention, the mounts of tissue sample including a genetically modified cell(s) to be implanted are determined from one or more of: Corresponding amounts of the therapeutic agent of interest routinely administered to such subjects based on regulatory guidelines, specific clinical protocols or population statistics for similar subjects. Corresponding amounts of the therapeutic agent such as protein of interest specifically to that same subject in the case that he/she has received it via injections or other routes previously. Subject data such as weight, age, physical condition, clinical status. Pharmacokinetic data from previous tissue sample which includes a genetically modified cell administration to other similar subjects. Response to previous tissue sample which includes a genetically modified cell administration to that subject.

In accordance with an aspect of some embodiments of the invention, only some of the DTMOs are used in a given treatment session. The remaining DTMOs may be returned to maintenance (or stored cryogenically or otherwise), for later use.

There is thus provided in accordance with an embodiment of the invention, a method of determining the amount of a therapeutic dermal micro-organ to be implanted in a patient, the method including determining a secretion level of a therapeutic agent by a quantity of the DTMO in vitro; estimating a relationship between in vitro production and secretions levels and in vivo serum levels of the therapeutic agent; and determining an amount of DTMO to be implanted, based on the determined secretion level and the estimated relationship. Optionally, the relationship is estimated based one or more factors chosen from the following group of factors:

a) Subject data such as weight, age, physical condition, clinical status;

b) Pharmacokinetic data from previous DTMO administration to other similar subjects; and c) Pharmacokinetic data from previous DTMO administration to that subject.

Optionally, the relationship is estimated based on at least two of said factors. Optionally, the relationship is based on three of said factors.

In an embodiment of the invention, determining an amount of a DTMO to be implanted in a patient is also based on one or both of:

corresponding amounts of the same therapeutic protein routinely administered to such subjects based on regulatory guidelines, specific clinical protocols or population statistics for similar subjects; and corresponding amounts of the same therapeutic agent specific to that same subject in the case the subject has received it previously via injections or other administration routes.

In an embodiment of the invention, the method includes preparing an amount of DTMO for implantation, in accordance with the determined amount.

There is also provided in accordance with an embodiment of the invention, method of adjusting the dosage of a therapeutic agent produced by a DTMO implanted in a subject and excreting a therapeutic agent, including (a) monitoring level of therapeutic agent in the subject; (b) comparing the level of agent to a desired level; (c) if the level is lower than a minimum level, then implanting additional DTMO; (d) and if the level is higher than a maximum level, then inactivating or removing a portion of the implanted DTMO. Optionally, the method includes periodically repeating (a)-(d). Alternatively or additionally, inactivating or removing consists of removing a portion of the implanted DTMO. Optionally, removing includes surgical removal. Alternatively or additionally, inactivating or removing includes inactivating. Optionally, inactivating includes killing a portion of the implanted DTMO. Optionally, inactivating includes ablating a portion of the implanted DTMO.

As described above with reference to FIG. 1, at least part of the process of sustaining the DMO during the genetic alteration, as well as the genetic alteration itself, may be performed in a bioreactor, as described below.

According to some embodiments of the invention, the bioreactor may have some or all of the following properties:

a) Allow for the provision of nutrients and gasses to the surfaces of the DMO so that they may diffuse into the DMO and the DMO may remain viable. Thus, significant areas and volumes of the DMO may not be blocked from coming into contact with a surrounding fluid.

b) Allow for the maintenance of the DMO at a desired temperature.

c) Allow for the maintenance of a desired pH and gas composition in the vicinity of the DMO.

d) Allow for the removal of waste products from the DMO and/or from the bio-reactor.

e) Allow for a simple method of inserting the genetically modifying vector without substantial danger that the inserting vector will contaminate the surroundings.

f) Allow for the removal of excess unused vector.

g) Allow for measurement of the amount of therapeutic agent generated.

h) Allow for removal of substantially sterile therapeutic agent.

i) Allow for easy insertion of the DMO and removal of all or measured amounts of DTMO.

Figure 22:
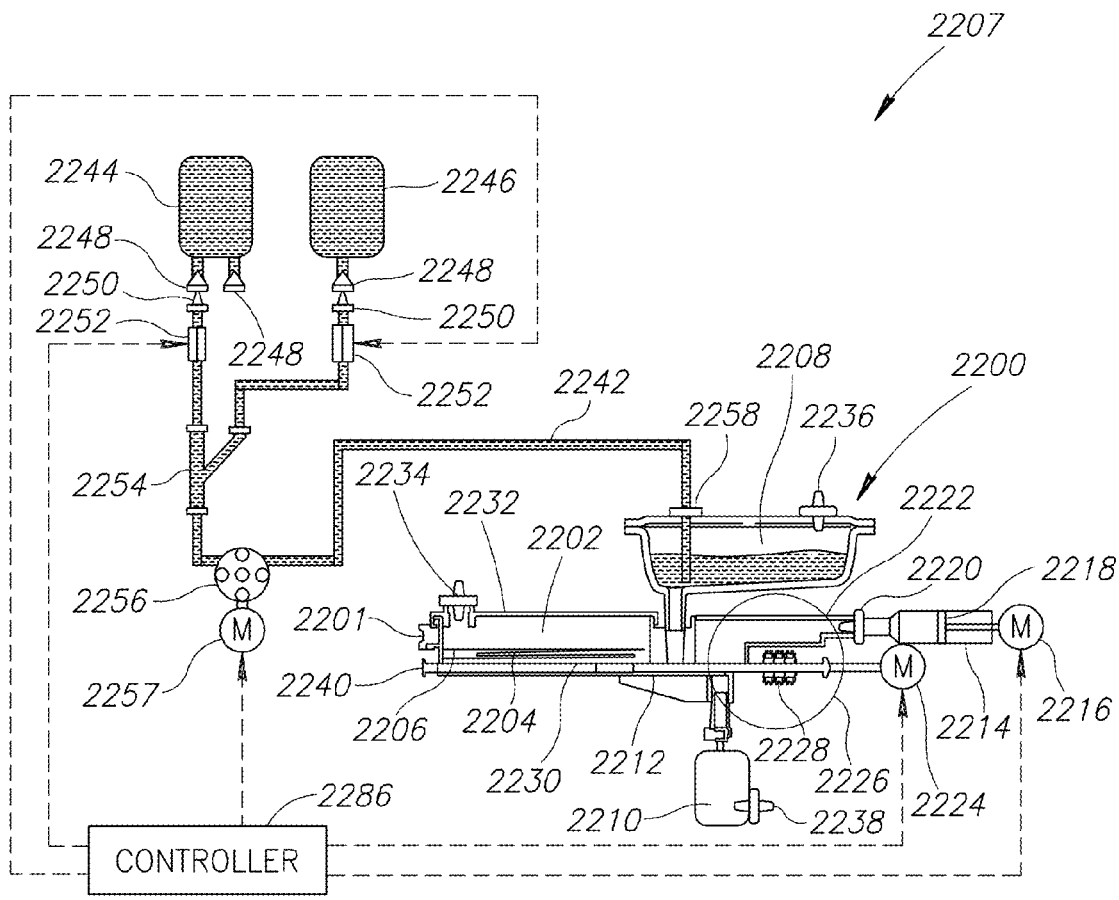
FIG. 22 is a schematic illustration of a system for processing a harvested DMO according to exemplary embodiments of the invention.

Reference in now made to FIG. 22, which schematically illustrates a system 2207 for processing a harvested DMO 2204, according to some exemplary embodiments of the invention.

According to some exemplary embodiments of the invention, system 2207 may include a bioreactor 2200 having one or more processing chambers 2202, each adapted to accommodate a DMO 2204. Bioreactor 2200, which in one exemplary embodiment has a number of chambers equal to the number of DMOs harvested from a particular subject, may be adapted to provide one or more of processing chambers 2202 with a suitable fluid or fluids, e.g., a growth medium, from a local fluid reservoir 2208 and/or discharge the fluid of one or more of processing chambers 2202, e.g., to a waste container 2210, as described below. The fluid may be supplied to reservoir 2208 via an inlet line 2242, e.g., connected by a sterile connector 2258 to reservoir 2208, as described below.

DMO 2204 may be transferred to chamber 2202 using a cutting tool used for harvesting DMO 2204, e.g., as described above. The DMO transfer into chamber 2202 may be preferably performed directly after harvesting DMO 2204 and while maintaining sterile conditions. Processing chamber 2202 may include a DMO insertion port 2201 adapted for receiving DMO 2204. For example, port 2201 may include a sterile septum interface capable of receiving a blunt cannula, e.g., a SafeLine® Injection Site marketed by B. Braun Medical Inc. Once the tip of the cutting tool is inserted through the septum, DMO 2204 may be gently flushed into chamber 2202 in a generally sterile manner, e.g., using a syringe connected to the back end of the cutting tool. According to one exemplary embodiment, DMO 2204 may be flushed into a medium bath 2206 within chamber 2202. Alternatively, if, for example, DMO 2204 was harvested with an inner guide, e.g., described above, a lid 2232 fitted over chamber 2202, e.g., as described below, may be removed, DMO 2204 may be gently removed from the inner guide and placed within chamber 2202, and lid 2232 may be returned and sealed over chamber 2202 to maintain sterility of chamber 2202.

Bioreactor 2200 may be adapted to apply, e.g., in a generally identical manner, one or more processes to DMOs being accommodated within at least some of the processing chambers. According to exemplary embodiments of the invention, bioreactor 2200 may be adapted to fluidically separate the contents of one or more of the processing chambers from the contents of one or more other processing chambers, as described below.

According to exemplary embodiments of the invention, bioreactor 2200 may also include a mechanism for controlling the flow of a fluid into and/or out of processing chamber 2202, as described below.

According to an exemplary embodiment, bioreactor 2200 may include a sterile buffer 2222 fluidically connected to a non-sterile syringe pump 2214, which may be adapted to inject air into buffer 2222 and/or discharge air from buffer 2222 in a sterile manner, e.g., via a sterile filter 2220, e.g. a 0.45 µm pore air filter. Bioreactor 2200 may also include a control valve 2212 able to be moved between at least four positions, e.g., an inlet-buffer position wherein inlet reservoir 2208 is fluidically connected to buffer 2222, an outlet-buffer position wherein waste container 2210 is fluidically connected to buffer 2222, a chamber-buffer position wherein chamber 2202 is fluidically connected to buffer 2222, and/or a no-connection position wherein buffer 2222, chamber 2202, inlet reservoir 2208, and waste container 2210 are fluidically disconnected from each other. A piston 2226 may connect between valve 2212 and a motor 2224 adapted to move valve 2212 between the different positions. Optionally, a bellows diaphragm 2228 may be fitted over piston 2226 such that there is substantially no transfer of non-sterile air from into the sterile buffer 2222, e.g., during motion of piston 2226.

System 2201 may also include a motor 2216 to actuate a plunger 2218 of syringe pump 2214. If bioreactor 2200 includes more than one chamber, then either one motor may be implemented for simultaneously actuating each one of the plungers associated with the chambers, or a plurality of motors may be implemented, each able to actuate one or more of the plungers.

According to exemplary embodiments of the invention, system 2201 may include a controller 2286 able to control the operation of motor 2216 and/or motor 2224, e.g., as described below.

According to exemplary embodiments of the invention, fluid from reservoir 2208 may be controllably transferred into chamber 2202, e.g., in order to fill chamber 2202. For example, controller 2286 may activate motor 2224 to position valve 2212 at the inlet-buffer position, and controllably activate motor 2216 such that syringe pump 2214 evacuates a predetermined quantity of air from buffer 2222. As a result a predetermined volume of fluid corresponding to the predetermined volume of air may be "drawn" from inlet reservoir 2208 into buffer 2222. Controller 2286 may then controllably activate motor 2224 to move valve 2212 to the chamber-buffer position, and controllably activate motor 2216 such that syringe pump 2214 discharges the fluid of buffer 2222 into chamber 2202. In a similar manner, the syringe pump and control valve may be controlled to discharge the contents of chamber 2202, or a partial amount thereof, into waste container 2210.

According to some exemplary embodiments of the invention, the fluid in chamber 2202 may be controllably stirred and/or mixed, e.g., in order to assist viral transduction and/or any other ex-vivo maintenance procedure applied to DMO 2204. For example, controller 2286 may controllably activate motor 2216 and/or motor 2224, e.g., as described above, to periodically discharge the fluid, or a part thereof, from chamber 2202 into buffer, and thereafter to inject the fluid in buffer 2222 back into chamber 2202.

According to some exemplary embodiments of the invention, air may be used to purge fluid located in one or more "passage lines", e.g., fluidically connecting between inlet reservoir 2208, waste container 2210 and/or chamber 2202, for example, in order to "flush" the passage lines after transferring fluid to/from chamber 2202, inlet reservoir 2208, and/ or buffer 2222. This aspect may be useful, for example, in order to reduce a "dead volume" of fluid, which may be "trapped" in one or more of the passage lines. For example, controller 2286 may controllably activate motor 2216 to move syringe plunger 2218 such that a predetermined volume of air is drawn into buffer 2222, before drawing the fluid from reservoir 2208 into buffer 2222. Buffer 2222 may have a geometry such that the air will rise above the fluid within buffer 2222, such that upon actuation of syringe pump 2214 the fluid in buffer 2222 may be discharged first, followed by the air, which will act to flush the passage lines of some or all of the fluid remaining therein.

According to some exemplary embodiments of the invention, a bottom surface 2230 of chamber 2202 may include a plurality of holes, or a mesh-like pattern, e.g., configured to enable the fluid to be transferred into and/or out of chamber 2202 in a substantially uniform manner, and/or to allow discharging substantially most of the fluid from chamber 2202 This configuration may also enable reducing the occurrence of "dead-spots", i.e., areas of chamber 2202 in which the fluid remains stagnant and/or is not refreshed.

According to some exemplary embodiments, lid 2232 may be a removable sterile lid, such as a membrane affixed by a detachable adhesive, silicon plug material, or the like. Lid 2232 may be adapted to maintain a sterile "barrier" between chamber 2202 and the environment. Optionally, a sterile air filter 2234, e.g., a 0.451 μm pore air filter, may be implemented to fluidically connect chamber 2202 and the environment, thus enabling equilibration of pressures while maintaining a sterile barrier between chamber 2202 and the environment. Alternatively, lid 2232 may include a "breathable" material, such that pressure equilibration may be enabled through lid 2232.

Reservoir 2208 and/or waste container 2210 may be commonly connected, e.g., via one or more manifolds (not shown), to one or more of processing chambers 2202 for a specific subject. Alternatively, inlet reservoir 2208 and/or waste container 2210 may be individually connected to each one of the processing chambers. Inlet reservoir 2208 and/or waste container 2210 may include a mechanism for equilibrating pressure in a sterile manner. For example, inlet reservoir 2208 and/or waste container 2210 may be fluidically connected to the environment via a sterile air filter 2236 and/or a sterile air filter 2238, respectively. Filter 2236 and/or filter 2238 may include, for example, a 0.45 μm pore air filter. Alternatively, waste container 2210 may include an expandable waste container, such that no pressure equilibration is required and, therefore, no sterile air filter need be used for it.

According to an exemplary embodiment of the invention, bioreactor 2200 may be adapted to enable direct injection of fluid or discharging of fluid to/from chamber 2202. A sampling septum port 2240 may be used, for example, for direct injection of viral vector fluid, or for sampling of growth medium to test for various bioreactor parameters, such as ELISA, glucose uptake, lactate production or any other indicative parameter. Septum port 2240 may include a standard silicon port adapted for needle insertion or a cannula port, e.g., as described above with reference to DMO insertion port 2201. A syringe (not shown) may be detachably inserted through septum port 2240. The syringe may be driven by a motor, e.g., similar to motor 2216, which may be activated manually or automatically, e.g., by controller 2286.

According to exemplary embodiments of the invention, at least some, and in some exemplary embodiments all, components of bioreactor 2200 may be maintained at predetermined conditions, e.g., incubator conditions, including a temperature of approximately 37.degree. C., a gaseous atmosphere of approximately 90-95% air and approximately 5-10% $CO_2$, and/or a relatively high degree of humidity, e.g., 85-100%. According to one exemplary embodiment, only chamber 2202 may be maintained in the incubator conditions. As described above, these incubator conditions may be required, e.g., for maintaining the vitality of the DMO tissue culture.

According to exemplary embodiments of the invention, a fluid supply arrangement may be implemented for supplying fluid to inlet line 2242 from at least one fluid tank, e.g., fluid tanks 2244 and 2246. In one exemplary embodiment, tanks 2244 and 2246 may contain the same fluid, e.g., a growth medium, in which case one tank may be used as a backup reservoir for the other tank. In another exemplary embodiment, tanks 2244 and 2246 may contain two different types of fluids, such as two types of growth medium to be used at different stages of DMO processing. Tank 2244 and/or tank 2246 may include a sterile air filter to equilibrate pressure in a sterile manner, e.g., as described above with reference to reservoir 2208. Alternatively, tank 2244 and/or tank 2246 may include a collapsible tank, e.g., a sterile plastic bag as is known in the art.

According to exemplary embodiments of the invention, each of tanks 2244 and 2246 may be fluidically connected to a combining connector 2254 via a valve 2252, e.g., a pinch valves, a septum port connector 2248 and a penetration spike 2250. Connector 2254 may include, for example a Y-shaped or a T-shaped connector as is known in the art. Valve 2252 may be adapted to control the flow of fluid from tank 2244 and/or tank 2246 to connector 2254. A pump, e.g., a peristaltic pump, 2256 may be located between connector 2254 and connector 2258, along inlet line 2242. Controller 2286 may be used to control the amount and/or flow-rate of the fluid provided to reservoir 2208 by controllably actuating motor 2257 and/or valves 2252.

According to one exemplary embodiment, the fluid contained within tanks 2244 and/or tank 2246 may have a storage shelf life of 9 days at refrigerated 4.degree. C. conditions. Thus, a refrigeration system (not shown) may be employed to maintain the fluid of tanks 2244 and/or 2246 at a temperature, which may be lower than the incubation temperature of reservoir 2208. Accordingly, inlet line 2242 may pass through an interface between refrigerator conditions to incubator conditions. After the shelf life has expired, tank 2244 and/or tank 2246 may be replaced by new tanks.

According to an exemplary embodiment, at least some of the elements of bioreactor 2200 to may be formed of disposable sterile plastic components. According to these embodiments, bioreactor apparatus 2200 may include a single-use sterilely packaged bioreactor apparatus, which may be conveyed to a DMO harvesting site and may be opened in a sterile environment and prepared on site such that growth medium is injected into each bioreactor chamber 2202. The tool used for harvesting the DMOs may be inserted through the DMO insertion ports 2201 to flush the DMOs into chambers 2202 in a sterile fashion, as described above. Bioreactor apparatus 2200 may be transported, e.g., under incubator conditions, to a processing site where it may be connected to other components of system 2207, e.g., connector 2258, motors 2216 and/or 2224, pinch valves 2252, and/or peristaltic pump 2256. Controller 2286 may then control the maintenance and transduction of the DMOs during the entire ex-vivo processing in which the DTMO is produced from the harvested DMO. The dosage needed for the specific subject may be determined by use of the pharmacokinetic model, e.g., as described herein. Bioreactor apparatus 2200 may then be detached from system 2207 and transported, e.g., under incubator conditions, to the site of implantation. In order to implant a specific DTMO, e.g., according to the implantation methods described above, bioreactor chamber 2202 for the specific DTMO may be opened by removing lid 2232 and the DTMO may be removed from the chamber.

EXAMPLES

Example 1

In vitro Secretion Levels of Human Erythropoietin by DTMO-hEPO

Experiments were conducted to assay the variability of in vitro hEPO secretion level between DTMOs-hEPO obtained from different human skin samples.

Experimental Procedure

Figure 4:
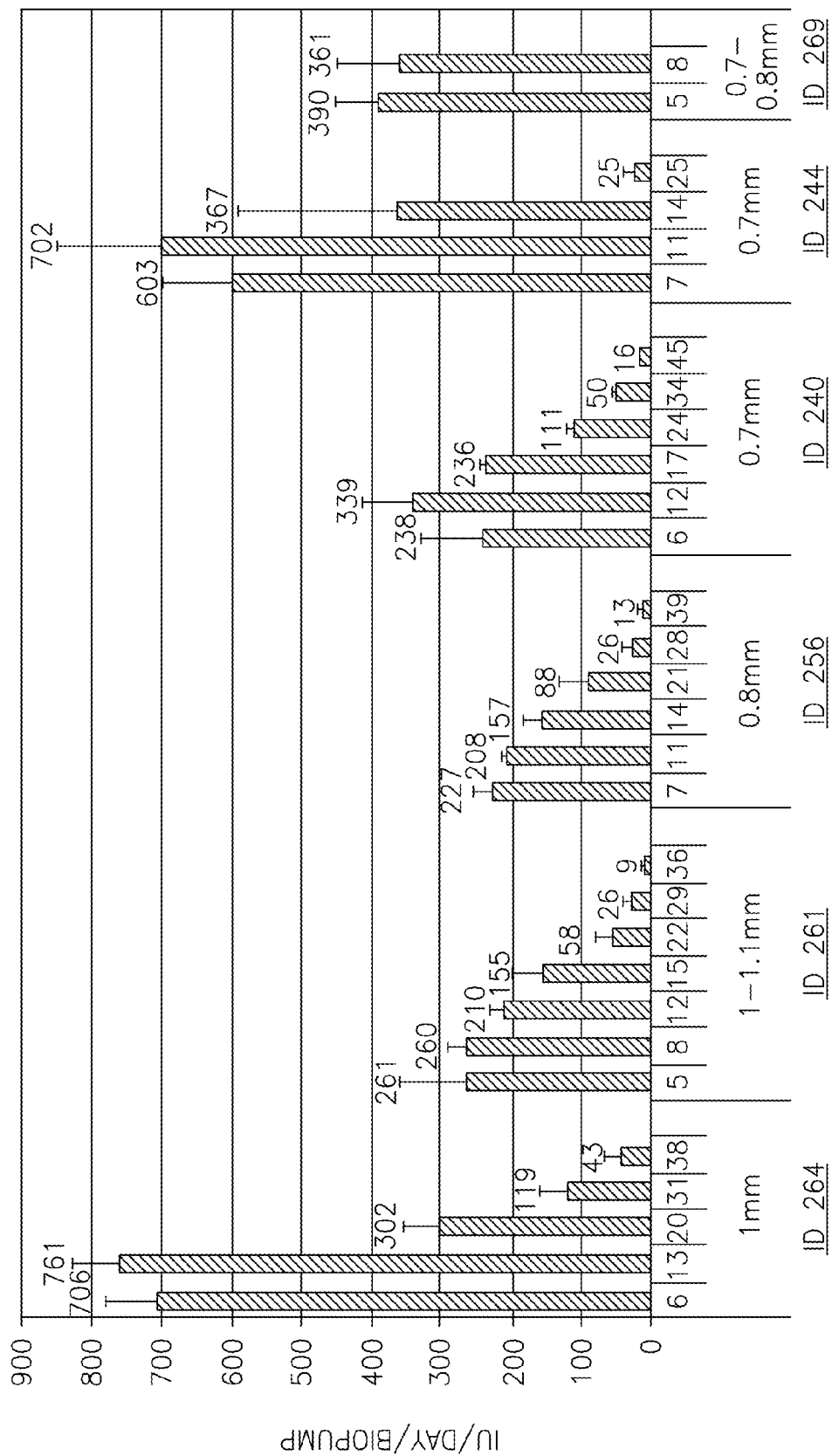
FIG. 4 is a schematic illustration of a graph showing secretion levels of human erythropoietin (hEPO) by DTMO-hEPO prepared from six different human skins.

DTMO-hEPO was prepared (in triplicates) from skin samples obtained from six different human subjects and hEPO secretion levels were measured at various point in time, as indicated in FIG. 4, after the viral vector was washed.

Experimental Results

The DTMO-hEPO secretion levels were similar among the different human skin samples. In addition, the DTMO-HEPO secretion levels were similar to the secretion levels of hEPO previously obtained from split thickness TMO-hEPO (data not shown).

Example 2

Histology

Figure 5:
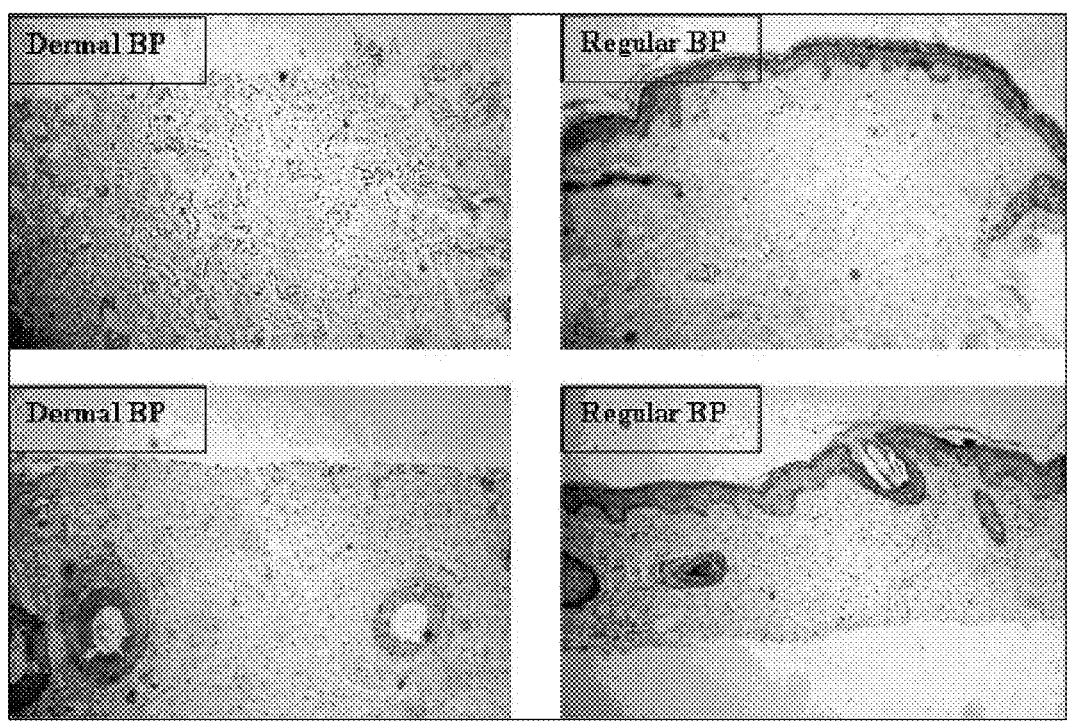
FIG. 5 shows histology of DTMO and split thickness skin TMO.

In order to verify that the DTMO contains mainly dermal components, a histological analysis was performed. MOs were prepared from either split thickness skin or dermal skin samples and histological analysis was performed by a dermato-pathologist. As can be seen on the left side of FIG. 5, the DTMO contains dermal layers and dermal components without residual basal and/or epidermal layers. In comparison, the split thickness TMO, shown on right side of FIG. 5, contains all the skin layers including the basal and epidermal layers.

Example 3

Immunocytochemistry Studies

Figure 6:
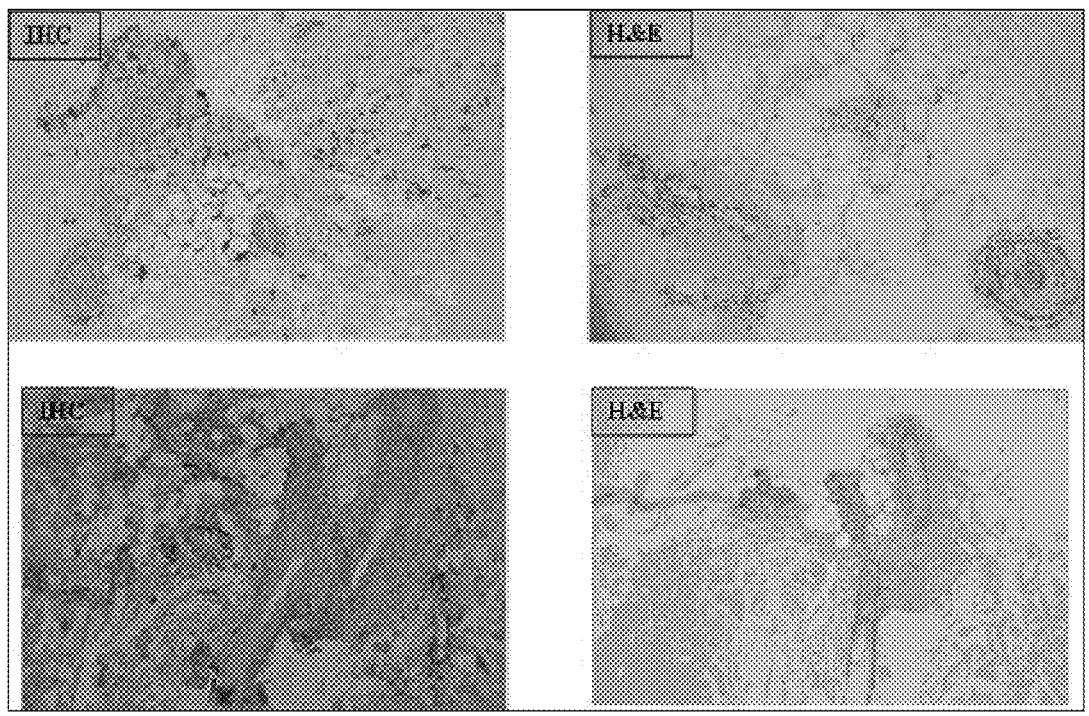
FIG. 6 shows Immunohistochemistry (IHC) and Hematoxylin & Eosin (H&E) staining of DTMO.

To study which cells are transduced in the DTMO-hEPO tissue, a histological immunohistochemistry analysis of DTMO-hEPO was performed on day 9 post-harvesting, using an anti-hEPO monoclonal antibody (1:20 dilution). Analysis revealed strong staining of dermal fibroblasts, as shown in FIG. 6. The staining was spread throughout the entire DTMO.

Example 4

Comparison of Long Term hEPO Hematopoietic Activity in SCID Mice Derived from DTMO-hEPO and Entire TMO An experiment was performed to examine and compare the long term effects of subcutaneously implanted DTMO-hEPO and Split thickness derived TMO-HEPO in SCID mice.

Experimental Procedure

Human DTMO-hEPO and human Split thickness derived TMO-hEPO were prepared and implanted subcutaneously in two groups of SCID mice (five mice per group). A control group was implanted with human DTMO and Split thickness derived TMO transduced with an Ad/lacZ viral vector.

Experimental Results

As is shown in FIG. 7, similar secretion levels and physiological response were identified in the two experimental groups while, as expected, the control group mice had no hEPO in their blood.

In all experimental groups, an elevation of hematocrit can be seen as early as 15 days post-implantation and is maintained for more than 5 months, while the MO/lacZ control mice do not show such an elevation in hematocrit level. DTMO-HEPO seems to result in similar secretion levels for similar time periods when compared to split thickness derived TMO-hEPO.

Example 5

DTMO-hEPO Do not Form Keratin Cysts when Implanted Sub-Cutaneously

Experimental Procedure

DTMO-hEPO and split thickness derived TMO-hEPO were implanted S.C. in SCID mice and keratin cyst formation was monitored by clinical and histological analysis.

Experimental Results

Figure 8:
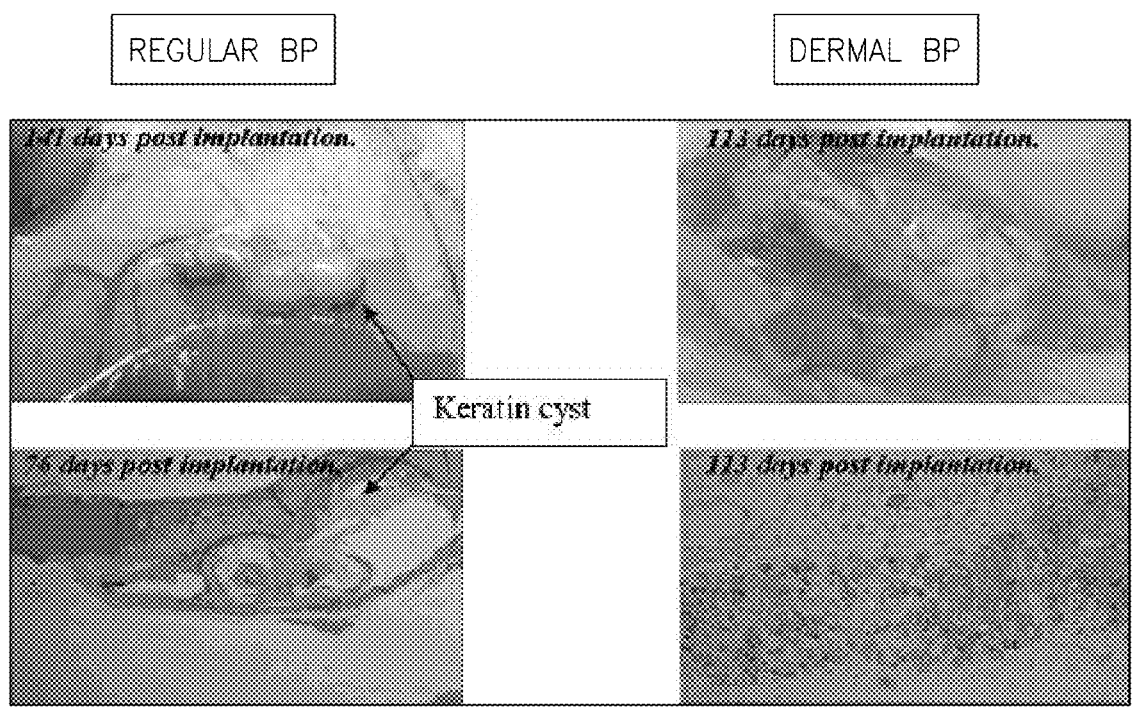
FIG. 8 demonstrates clinical and histological analysis of DTMO-hEPO and split thickness skin TMO-hEPO implanted subcutaneously in SCID mice.

As can be clearly seen in FIG. 8, keratin cyst formation was observed while implanting the split thickness derived TMO-hEPO 76 and 141 days post implantation. In contrast, no cyst formation was observed in SCID mice with the DTMO-hEPO 113 days post implantation.

Example 6

Split Thickness Derived and DMO Integration in Healthy Human Subjects

Experimental Procedure

Human Dermal MO and human split thickness derived Split thickness derived TMO were obtained using a commercially available dermatome (Aesculap GA 630). Prior to harvesting, topical and local anesthesia for both the donor and recipient site were performed using Emla lotion (topical anesthesia) and subcutaneous injections of Marcain+Adrenalin (local anesthesia).

Two types of skin samples were harvested in order to produce human Dermal MO and human split thickness derived MO. For human split thickness derived MO, a strip of healthy skin was excised from the lower part of the abdomen. From this skin section, six linear MOs were prepared as previously described. Simultaneously, slits of specific dimensions were made in the implantation site using an adjustable slit maker, and MOs were grafted shortly after into the skin slits. For preparing Human Dermal MO, skin was harvested in two steps. First, a skin flap of 200 μm in depth was harvested and kept on moist gauze. From this harvest site, a 1 mm deep dermis skin strip was harvested. Following skin harvesting, the 200 μm skin flap was placed back on the donor site serving as a biological dressing. From the dermis strip harvested above, four dermal MOs were prepared utilizing an identical procedure as for the split thickness derived Split thickness derived TMO MO. The human Dermal MO were implanted subcutaneously shortly after, using a trocar. The donor and implantation sites were dressed using Bioclusive® transparent membrane (Johnson & Johnson, USA). After one week the dressing was changed and the implants were examined to check graft integration. Two to three weeks following the MO implantation, the scheduled abdominoplasty procedure was performed and a section of skin, including the graft and implantation area was excised. A clinical evaluation was performed on the graft area including photographs and histological examination to determine MO integration.

Experimental Results

Figure 9:
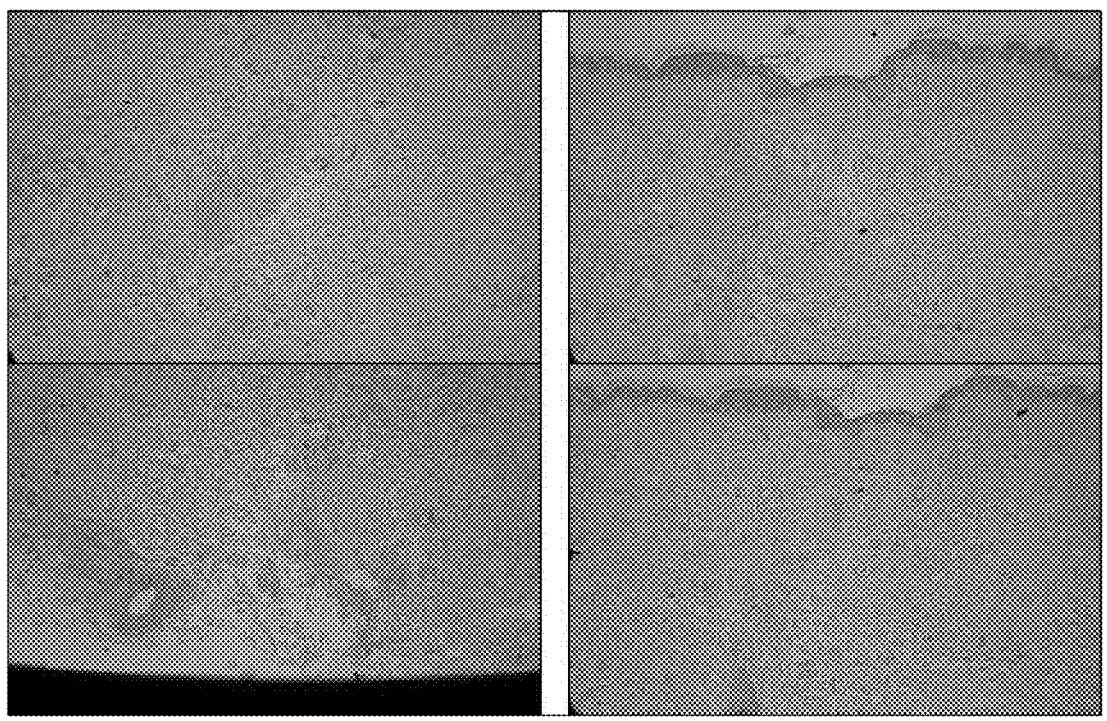
FIG. 9 shows Histological analysis of skin MOs grafted in skin slits (split thickness skin MO, right) or implanted S.C. (DMO, Left) 17 days post implantation in healthy volunteers.

A clinical inspection, which was performed one week after implantation, and histological analysis, which was performed soon after abdominoplasty (2-3 weeks after grafting), revealed excellent integration of the grafted MOs into the skin slits and at the dermal MOs subcutaneous implantation sites (FIG. 9). No indication of inflammation or swelling was found on either split thickness derived MOs that were implanted into the slits or Dermal Mos that were implanted subcutaneously.

Example 7

Autologous Implantation of Miniature Swine Skin Linear Split Thickness TMOs, Expressing Human Erythropoietin (hEPO into Immuno Competent Animals)

Linear (30.6 mm long and 0.6 micrometer wide) miniature swine (Sinclar swine) skin micro-organs were prepared from fresh skin tissue samples obtained from live animals under general anesthesia procedures. Tissue samples of 0.9-1.1 mm split skin thickness (depth) were removed using a commercial dermatome (Aesculap GA630) and cleaned using DMEM containing glutamine and Pen-Strep in Petri dishes (90 mm).

In order to generate the linear micro-organs, the above tissue samples were cut by a press device using a blade structure as described above, into the desired dimensions: 30.6 mm times.600 micrometers. The resulting linear micro-organs were placed, one per well, in a 24-well micro-plate containing 500 μl per well of DMEM (Biological Industries—Beit Haemek) in the absence of serum under 5% $CO_2$ at 37.degree. C. for 24 hours. Each well underwent a transduction procedure in order to generate a miniature swine skin therapeutic micro-organ (pig skin-TMO) using an adeno viral vector (1.times.10.sup.10 IP/ml) carrying the gene for human erythropoietin (Adeno-hEPO) for 24 hours while the plate was agitated. The medium was changed every 2-4 days and analyzed for the presence of secreted HEPO using a specific ELISA kit (Cat. #DEP00, Quantikine IVD, R&D Systems).

Figure 3A:
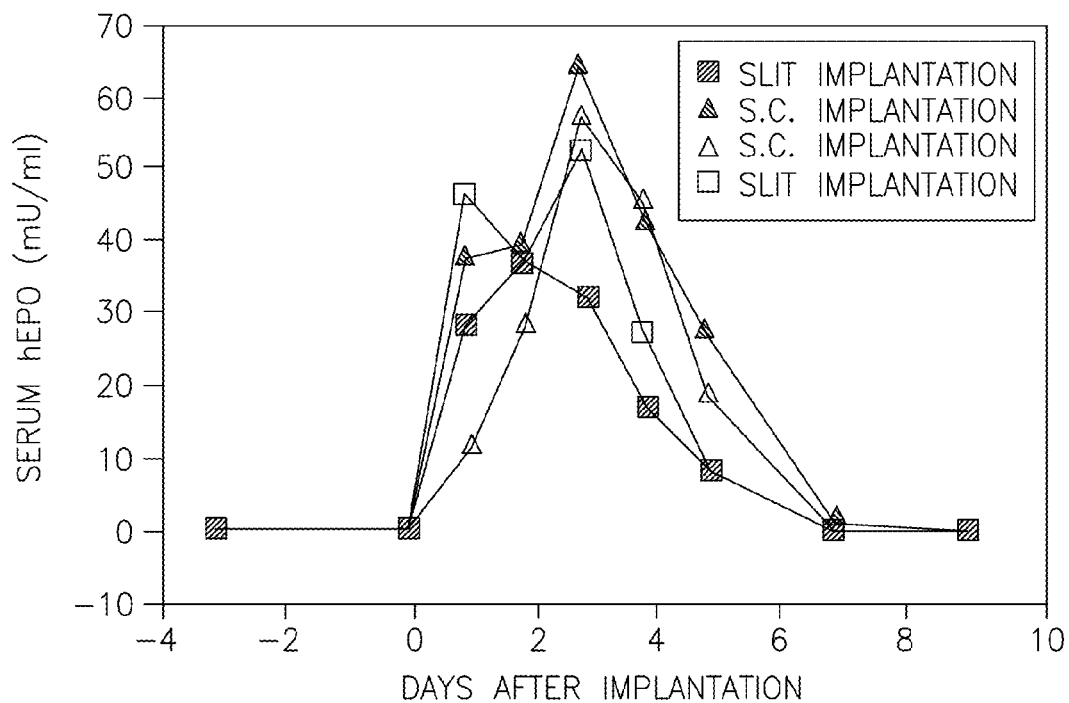
FIGS. 3A and 3B show, respectively, elevated serum hEPO levels determined by an ELISA assay and reticulocyte count elevation after autologous TMO implantation in a miniature swine, in accordance with an embodiment of the invention.
Figure 3B:
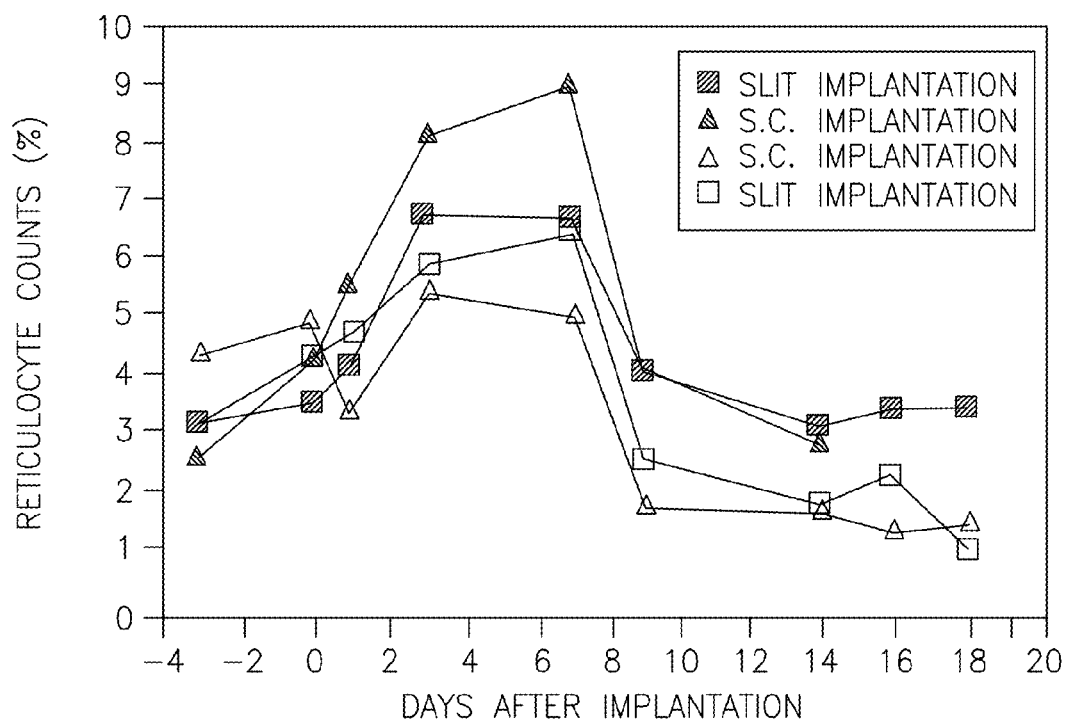

The above described miniature swine skin hEPO linear TMOs were implanted both sub-cutaneously and grafted as skin grafts in several immune competent miniature swines (in two of the miniature swine, the TMOs-hEPO were implanted subcutaneously, and in two different miniature swine, TMOs-hEPO were grafted in 1 mm deep slits). A sufficient number of TMOs-hEPO were implanted in each miniature swine so that their combined pre-implantation secretion level in each pig was approximately 7 micrograms per day. Elevated serum HEPO levels (FIG. 3A) determined by an ELISA assay and reticulocyte count elevation were obtained for seven days after implantation.

It will thus be clear, the present invention has been described using non-limiting detailed descriptions of embodiments thereof that are provided by way of example and that are not intended to limit the scope of the invention. For example, only a limited number of genetic changes have been shown. However, based on the methodology described herein in which live tissue is replanted in the body of the patient, and the viability of that tissue in the body after implantation, it is clear that virtually any genetic change in the tissue, induced by virtually any known method will result in secretions of target proteins or other therapeutic agents in the patient.

Variations of embodiments of the invention, including combinations of features from the various embodiments will occur to persons of the art. The scope of the invention is thus limited only by the scope of the claims. Furthermore, to avoid any question regarding the scope of the claims, where the terms "comprise" "include," or "have" and their conjugates, are used in the claims, they mean "including but not necessarily limited to".

What is claimed is:

1. A method of delivering interferon to a subject comprising implanting into or underneath the skin at least one genetically modified dermal micro-organ that expresses and secretes at least one recombinant gene product or at least a portion of said at least one recombinant gene product,
   a. wherein said at least one recombinant gene product comprises interferon;
   b. wherein said genetically modified dermal micro-organ is autologous with said subject;
   c. wherein said dermal micro-organ is an explant of living tissue consisting essentially of a plurality of dermal components and lacking a complete epidermal layer that substantially maintain the micro-architecture and three-dimensional structure of the dermal tissue from which they are obtained, and having dimensions selected so as to allow passive diffusion of adequate nutrients and gases to cells of said dermal micro-organ and diffusion of cellular waste out of said cells so as to minimize cellular toxicity and concomitant death due to insufficient nutrition and accumulation of waste in said dermal micro-organ; and
   d. wherein at least some of the cells of said genetically modified dermal micro-organ express and secrete at least a portion of said interferon;
   wherein said implanting of said at least one genetically modified dermal micro-organ delivers interferon to said subject.

2. The method of claim 1, wherein said interferon is selected from the group consisting of interferon α, interferon β and interferon γ.

3. The method of claim 1, wherein said at least one genetically modified dermal micro-organ is a linear micro-organ.

4. The method of claim 3, wherein said linear micro-organ remains in a linear form after said implanting.

5. The method of claim 1, wherein said at least one genetically modified dermal organ includes at least part of the cross-section of the dermis.

6. The method of claim 1, wherein said at least one genetically modified dermal organ includes fat tissue.

7. The method of claim 1, wherein said at least one genetically modified dermal organ comprises an in-vivo demarcation.

8. The method of claim 7, wherein said in-vivo demarcation comprises an ink or stain on the peripheral surface of said micro-organ.

9. The method of claim 7, wherein said in-vivo demarcation comprises a green fluorescent protein (GFP) gene or a luciferase reporter gene expressed by said micro-organ.

10. The method of claim 1, wherein said at least one genetically modified dermal organ is 5-100 mm in length.

11. The method of claim 10, wherein said at least one genetically modified dermal organ is 10-60 mm in length.

12. The method of claim 11, wherein said at least one genetically modified dermal organ is 20-40 mm in length.

13. The method of claim 1, wherein at least one dimension of the cross-section of said at least one genetically modified dermal organ is 0.5-3.5 mm.

14. The method of claim 1, wherein said implanting under the skin is subcutaneous implanting.

15. The method of claim 1, wherein said delivery of interferon increases serum interferon in said subject.

* * * * *